(12) United States Patent
Lo

(10) Patent No.: US 12,036,259 B2
(45) Date of Patent: Jul. 16, 2024

(54) METHOD OF TREATMENT OF CANCERS

(71) Applicant: Shui Yin Lo, Arcadia, CA (US)

(72) Inventor: Shui Yin Lo, Arcadia, CA (US)

( * ) Notice: Subject to any disclaimer, the term of this patent is extended or adjusted under 35 U.S.C. 154(b) by 0 days.

(21) Appl. No.: 18/388,167

(22) Filed: Nov. 8, 2023

(65) Prior Publication Data

US 2024/0075091 A1 Mar. 7, 2024

Related U.S. Application Data

(63) Continuation-in-part of application No. 16/388,808, filed on Apr. 18, 2019, now abandoned.

(51) Int. Cl.
| | |
|---|---|
| *A61K 36/00* | (2006.01) |
| *A61K 36/232* | (2006.01) |
| *A61K 36/282* | (2006.01) |
| *A61K 36/34* | (2006.01) |
| *A61K 36/355* | (2006.01) |
| *A61K 36/481* | (2006.01) |
| *A61K 36/536* | (2006.01) |
| *A61K 36/539* | (2006.01) |
| *A61K 36/65* | (2006.01) |
| *A61K 36/896* | (2006.01) |
| *A61K 36/902* | (2006.01) |
| *A61K 36/9066* | (2006.01) |
| *A61P 35/00* | (2006.01) |

(52) U.S. Cl.
CPC .......... *A61K 36/539* (2013.01); *A61K 36/232* (2013.01); *A61K 36/282* (2013.01); *A61K 36/34* (2013.01); *A61K 36/355* (2013.01); *A61K 36/481* (2013.01); *A61K 36/536* (2013.01); *A61K 36/65* (2013.01); *A61K 36/896* (2013.01); *A61K 36/902* (2013.01); *A61K 36/9066* (2013.01); *A61P 35/00* (2018.01)

(58) Field of Classification Search
CPC ....................................................... A61P 35/00
See application file for complete search history.

*Primary Examiner* — Qiuwen Mi
(74) *Attorney, Agent, or Firm* — Elizabeth Yang

(57) ABSTRACT

A method for treatment of cancer, the method comprises preparing a solid water particle solution and a Chinese herb composition; administering a predetermined amount of the solid water particle solution three times a day and a predetermined amount of the Chinese herb composition two times a day, and continue the administering for 14 days to complete a course of treatment; and determining healing effects of the cancer by taking blood test, wherein the Chinese herb composition consists of *Scutellaria barbata, Lobelia chinensis, Paris polyphylla, Prunella vulgaris, Artemisia capillaris*, Chinese Thorawax Root, White Peony Root, *Houpoea officinalis*, Indian Bread peel, Asiatic Plantain Seed, *Astragalus membranaceus, Angelica sinensis*, Dried Tangerine Peel, Common Burreed Rhizome, Blue Turmeric Rhizome, and Japanese Honeysuckle Stem.

14 Claims, 18 Drawing Sheets

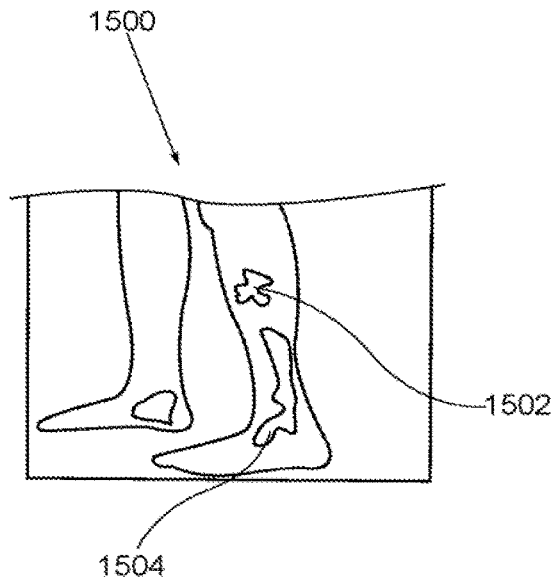 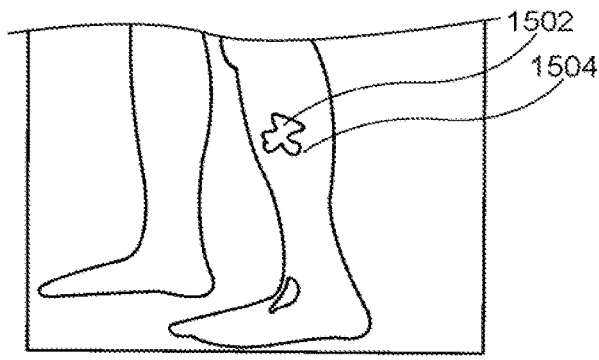
FIG. 15A  FIG. 15B
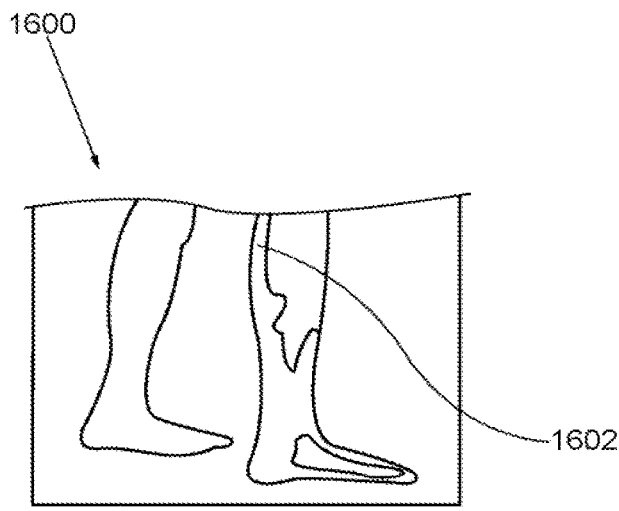 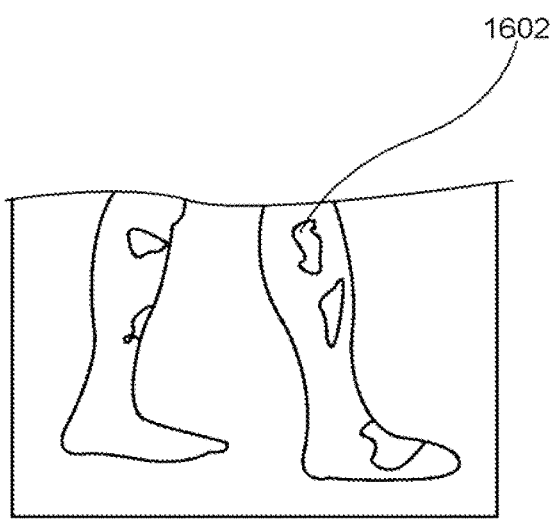
FIG. 16A  FIG. 16B

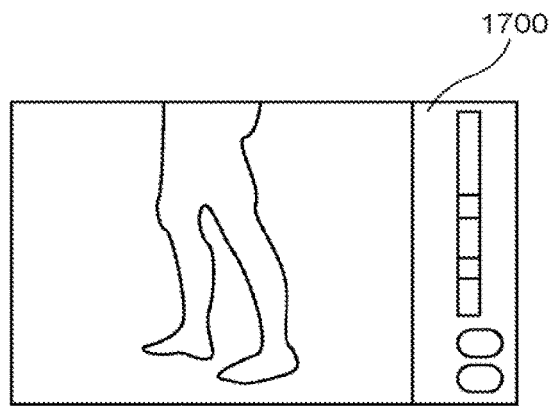
FIG. 17A
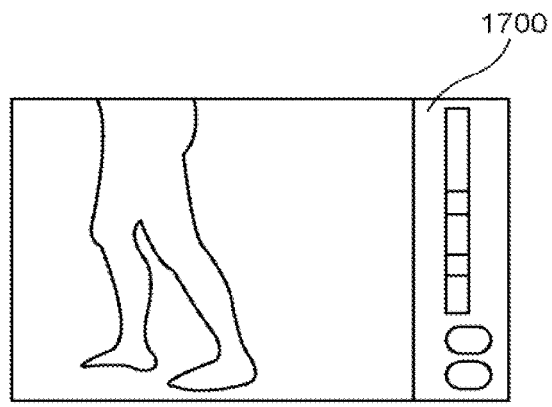
FIG. 17B
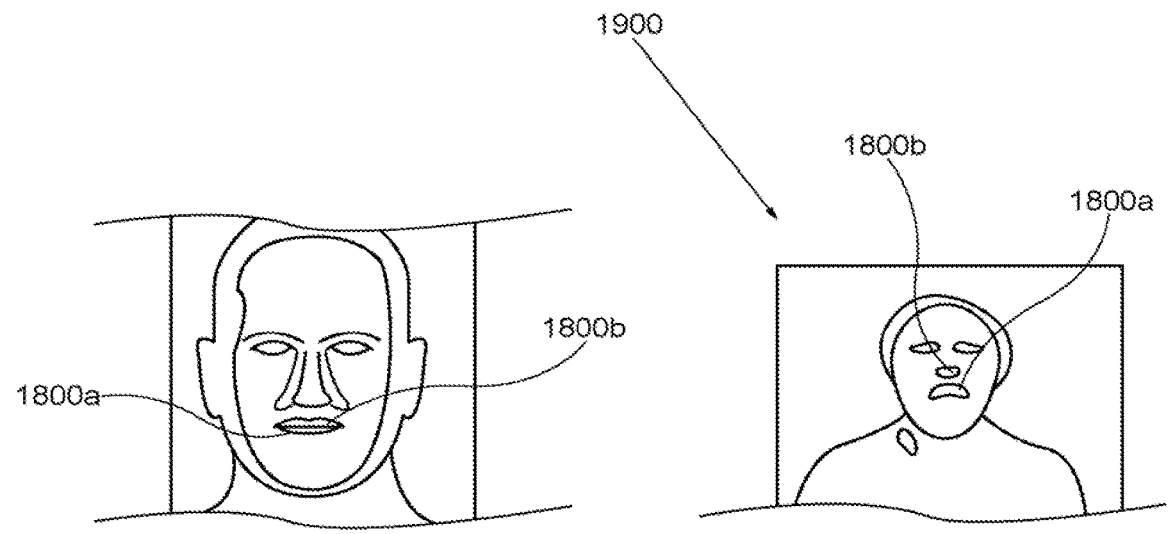
FIG. 18
FIG. 19

METHOD OF TREATMENT OF CANCERS

CROSS-REFERENCE TO RELATED APPLICATIONS

This application is a continuation-in-part of U.S. patent application Ser. No. 16/388,808 filed on Apr. 18, 2019 which provisional application is incorporated by reference herein in its entirety.

FIELD OF THE INVENTION

The present invention relates generally to a method of treatment of cancer through the combination of traditional Chinese medicine and solid water particle invented by the applicant. More so, a method for treatment of cancer is configured to combine a traditional Chinese medicine composition and solid water particle to treat cancer, especially for biliary cancer or liver cancer.

BACKGROUND OF THE DISCLOSURE

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Nowadays, there are some ways to treat cancers happened in the human body. The common ways for that is chemotherapy.

However, is also very harmful to the human body, while in traditional Chinese medicine, the traditional Chinese medicine specialist usually will provide a different way than in Western Medicine for treating these kinds of diseases.

Therefore, the applicant, after research, has invented a way of therapy in conjunction with Chinese medicine, in order to avoid that therapy itself causes great harm to human body.

BRIEF SUMMARY OF THE DISCLOSURE

One objective of the present invention is to provide a method treatment of cancer through the combination of traditional Chinese medicine to reduce the harm that would be caused to human body.

Another objective of the present invention is to provide a new way of utilizing solid water particle treatment to treat the cancer.

To achieve the objects above, the present invention provides a method of treatment of cancer, the method comprising:

preparing a solid water particle solution and a Chinese herb composition;
administering a predetermined amount of the solid water particle solution at least two times a day and a predetermined amount of the Chinese herb composition at least two times a day, and continue the administering for 14 days to complete a course of treatment; and
determining healing effects of the cancer by taking blood test,
wherein the Chinese herb composition consists of *Scutellaria barbata, Lobelia chinensis, Paris polyphylla, Prunella vulgaris, Artemisia capillaris*, Chinese Thorawax Root, White Peony Root, *Houpoea officinalis*, Indian Bread peel, Asiatic Plantain Seed, *Astragalus membranaceus, Angelica sinensis*, Dried Tangerine Peel, Common Burreed Rhizome, Blue Turmeric Rhizome, and Japanese Honeysuckle Stem.

In another aspect, wherein the cancer is a biliary cancer or liver cancer.

In another aspect, wherein when administering the predetermined amount of Chinese herb composition, also administering the predetermined amount of the solid water particle solution.

In another aspect, wherein a ratio of the predetermined amount of the solid water particle solution to the predetermined amount of Chinese herb composition is 5:1.

In another aspect, wherein a weight of every Chinese herb in the Chinese herb composition is between 4 and 5 grams.

In another aspect, wherein a way for administering the predetermined amount of the solid water particle solution is selected from a group consisting of oral administration and intravenous administration.

In another aspect, wherein the predetermined dosage of the solid water particle solution is at least 300 grams.

In another aspect, wherein the predetermined dosage of the Chinese herb composition is at least 60 grams.

In some embodiments, the present application further comprising: repeating the course of treatment until the healing effects of the cancer indicate a patient is not suffering from the cancer.

In some embodiments, the present application further comprising: proceeding with another course of treatment if the healing effects of the cancer do not indicate a patient is recovering from the cancer.

In another aspect, wherein the another course of treatment comprises administering a predetermined amount of the solid water particle solution five times a day and a predetermined amount of the Chinese herb composition two times a day, and continue the administering for 14 days.

In another aspect, wherein the oral administration comprises a liquid, a capsule, or a gel consisting of solid water particles.

In another aspect, wherein the intravenous administration comprises an intravenous injection consisting of solid water particles.

In another aspect, wherein healing effects are determined by taking blood test.

In another aspect, wherein the course of treatment comprises administering a predetermined amount of the solid water particle solution three times a day and a predetermined amount of the Chinese herb composition two times a day, and continue the administering for 14 days.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which:

FIGS. 15A and 16A illustrate exemplary thermographs of the gallbladder meridian for an internally inflamed gallbladder before administering solid water particles, in accordance with an embodiment of the present invention;

FIGS. 15B and 16B illustrate exemplary thermographs of the gallbladder meridian for an internally inflamed gallbladder shown in FIGS. 15A and 16A, fifteen minutes after administering solid water particles, in accordance with an embodiment of the present invention;

FIGS. 17A and 17B illustrate exemplary correspondence of color scheme and temperature of the thermographs shown in FIGS. 16A and 16B, in accordance with an embodiment of the present invention;

FIG. 18 illustrates an idealized large intestine meridian viewed through an infrared imaging device, in accordance with an embodiment of the present invention;

FIG. 19 illustrates an exemplary thermograph of the large intestine meridian shown in FIG. 18, in accordance with an embodiment of the present invention;

DETAILED DESCRIPTION OF THE INVENTION

Figure 1:
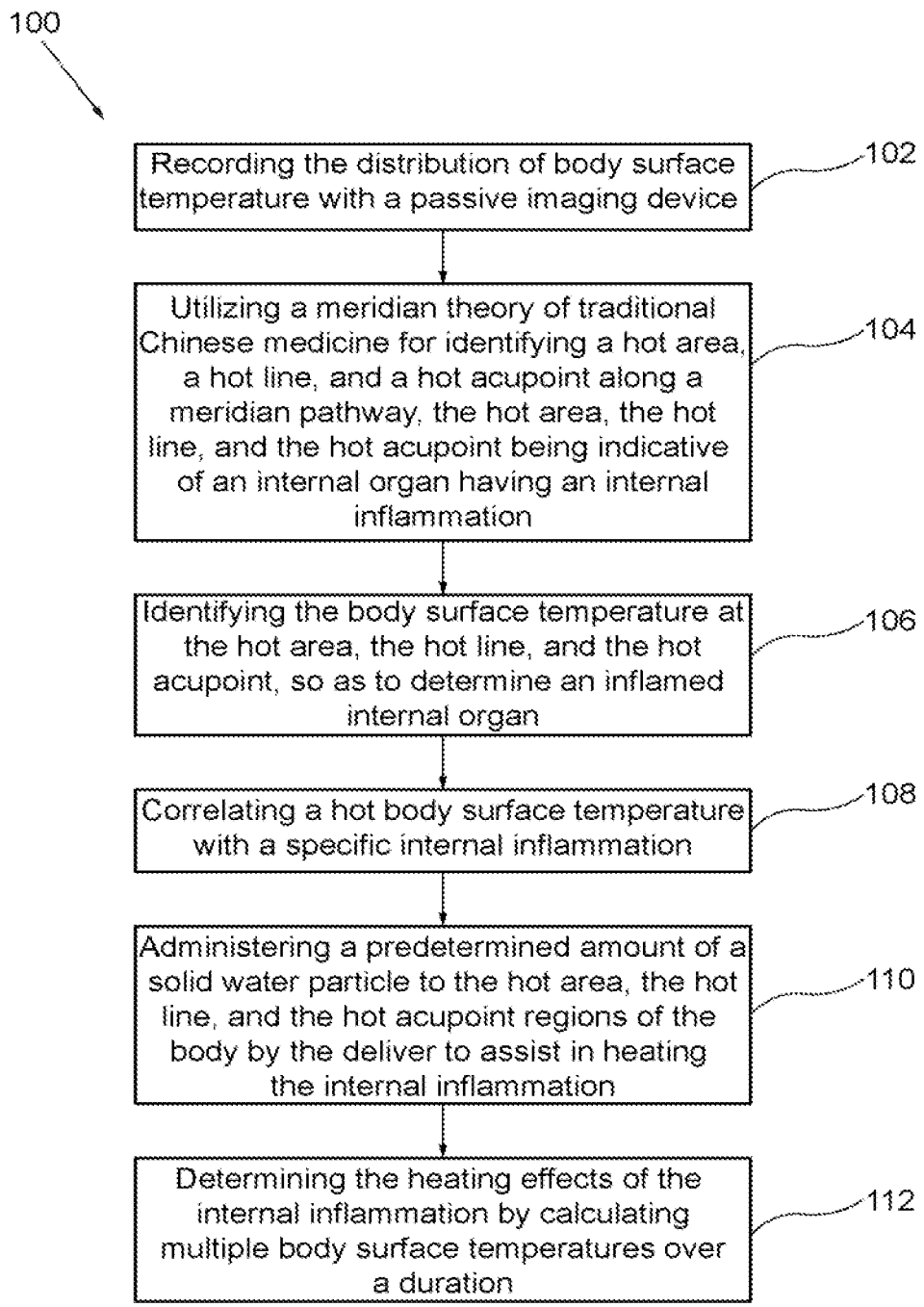
FIG. 1 illustrates a flowchart diagram of an exemplary method for detection, treatment, and reduction of internal inflammation, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "first," "second," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. § 112.

In one embodiment of the present invention presented in FIGS. 1-29B, a method 100 for detection and reduction of internal inflammation of the prevention of cancer in an organ 212, and prevention of cardiac vascular diseases combine passive (multiple) images 204 showing the temperature of the body surface and a meridian theory of traditional Chinese medicine. The method provides the steps of: recording the distribution of body surface temperature with a passive imaging device 202 (block 102), such as an infrared imaging device; utilizing a meridian theory of Chinese medicine for identifying at least one hot area 206, at least one hot line 208, and at least one hot acupoint 210 along a meridian pathway (block 104); identifying the body surface temperature at the hot area 206, the hot line 208, and the hot acupoint 210, so as to determine an inflamed internal organ 212 (block 106); correlating a hot body surface temperature with a specific internal inflammation (block 108); administering predetermined amounts of solid water particles to the hot area 206, the hot line 208, and the hot acupoint 210 regions of the body by the delivery to assist in healing the internal inflammation (block 110); and determining healing effects of the internal inflammation by calculating multiple body surface temperatures over a duration (block 112).

In some embodiments, the method 100 utilizes a passive imaging device 202 for imaging the body surface temperature to indicate internal organ inflammations and overactive systems. Those skilled in the art will recognize that the commonly used imaging methods used to discover diseases inside a human body such as X-ray, CT-scan, are invasive, and causes damage inside the human body. Ultrasound and MM are much less harmful, and still, involve shaking internal organs or protons. So they are active device and not a passive device. The non-invasive and passive imaging methods are rare. Infrared imaging is one such method. It does not emit any radiation, or even infrared itself. It is a passive device. Thus, the passive imaging device 202 just records the infrared emitted from the surface of the body, such as inflammation on the surface of the skin to produce multiple images 204, which are used to administer solid water particles (SWP).

The method 100 also utilizes a meridian theory of traditional Chinese medicine for identifying the hot region which comprises at least one hot area 206, at least one hot line 208, and at least one hot acupoint 210 along the meridian pathway. Thus, if a meridian theory in Chinese medicine is combined with the inflamed internal organs 212, the body surface temperature phenomena, especially and the heat on the meridian lines near the surface of the body is synergized with the phenomena of internal inflamed organs 212. Knowing that meridian lines carry heat from inflamed, damaged, or potentially cancerous inflamed internal organs 212, the surface body temperature is positively correlated to the temperature of inflamed internal organs 212 where the meridian lines pass. In this manner, detection of internal inflammation in the inflamed internal organs 212 is facilitated.

In one possible embodiment of the method 100, the hot area 206, the hot line 208, and hot acupoint 210 are identified to define a specific point on the surface of the body located on the meridian pathway. These hot regions may also be defined as a point on the body into which an acupuncture needle may be inserted for treatment, as is performed in traditional Chinese medicine. Often, these hot regions on the surface of the body receive heat from the inflamed internal organs; thereby providing an indication of inflammation or preliminary stages of cancer of an internal organ.

Thus, a correlation between the hot area 206, the hot line 208, and the hot acupoint 210 help to determine the type of internal ailment at the internal organs and regions of the body. This is because the meridian pathways serve as an optical fiber that channels the heat of internal organs to the surface of the body. The higher body surface temperature indicated by the hot regions is thus, a reflection of the temperature of the internal organs where the meridian pathways pass through.

Specifically, the hot body surface temperature along the meridian pathways and acupoint are an indication of the inflammation or cancer of the inflamed internal organs 212. Those skilled in the art will recognize that inflamed or potentially cancerous internal organs emit hot infrared radiation, which is transmitted preferentially along the meridian pathways and peaks at known acupoints that are close to the surface of the body. Thus, method 100 measures the degree of the ailment of the inflamed internal organ 212 by the quantitative temperature at the acupoint. In essence, internal organ abnormalities can be revealed by taking thermographs of the body and corresponding problematic organs with the meridian pathways.

Those skilled in the art will recognize that the meridian pathway comprises a discrete, network that connects different internal organs of the body. The meridian pathway may also be defined as a line of energy flow from an internal organ to the surface of the body. The meridian pathway is determined through traditional Chinese medicinal means.

Once the hot regions have been discerned, the treatment commences with predetermined amounts of solid water particles (SWP). The SWP functions to unblock the meridian channels and allow qi and blood to flow freely to the inflamed area. In one embodiment, the SWP consists of only pure water molecules and no other chemicals and generally does not have harmful side effects. The SWP may include, without limitation, stable water clusters, polydihydrogenoxide, and IE.

The method 100 also comprises another step: administering predetermined amounts of solid water particles to the hot area 206, the hot line 208, and the hot acupoint regions 210 of the body by the delivery (block 110). This may help in healing the internal inflammation. The delivery means of the SWP comprises at least one of the following: oral administration, topical administration, vapor administration, and intravenous administration.

Figure 3:
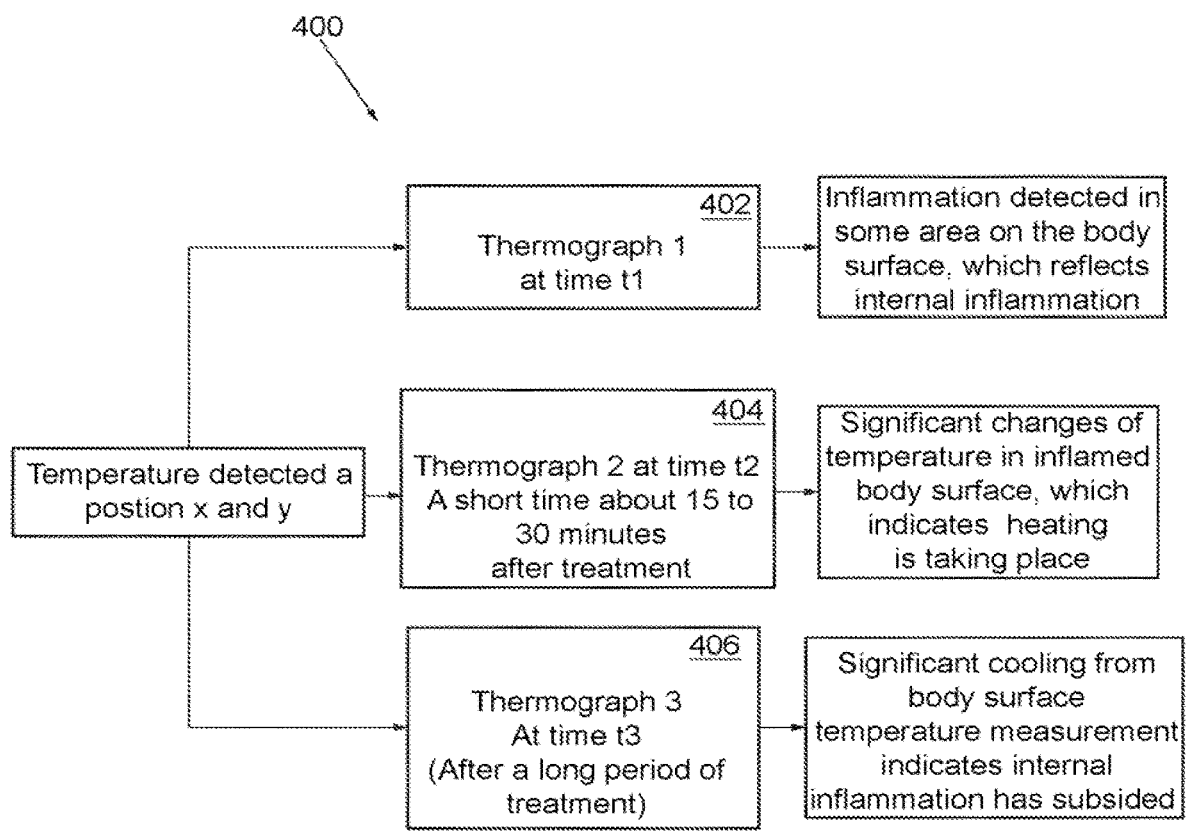
FIG. 3 illustrates a diagram illustrating an exemplary process of the correlation between the hot regions of the body with internal inflammations and cancers, in accordance with an embodiment of the present invention.

Referring to FIG. 3 of the drawings, the healing effects are discerned by calculating multiple passive images 204 over a duration. The duration of the hot region indicates the stage at which healing is occurring. Specifically, Detection of healing effect from treatment: In order to see the effect of healing from the treatment, it is necessary to take more than one set of thermographs. The first set of thermographs at time $t_1$ is to detect the inflammation of internal parts. The temperature is given by the passive image at the position x, and y at time $t_1$ for α, which can be an area, line, or points. The accuracy of the current commercial infrared camera system is less than 0.1° C.

Then after a short duration, about 15 minutes to 30 minutes another set of thermographs are taken at time $t_2$. Significant changes of temperature in hot areas 206, hot lines 208, and hot acupoints 210 indicating the healing has taken. The change of temperature at x,y, is their differences. The statistical fluctuation of skin temperature is about 0.1° C. So if the absolute value of the temperature is greater than 0.3° Celsius. Then the change of temperature is three standard deviations away. Instead of measuring and calculate each time, the color scheme of the passive image is beneficial. The change of color is about 1° Celsius. There may be three shades of color. So if we detect the change of shade of color the change is statistically significant.

The solid water particles discussed above function to unblock the meridian channel and allow qi and blood to flow freely to an inflamed area, which generally gets even hotter. If the inflammation is not serious, healing occurs. In 15 minutes, inflammation is generally reduced. If the inflammation is serious, the healing occurs but is generally not sufficient for complete healing. So the inflamed area becomes hotter after 15 minutes. Whether the area gets hotter or colder, healing has occurred. But for the healing to be successful, it should cool down eventually. So often time the third set of thermograph is needed to confirm that healing succeeds, where the difference of temperature is seen between the third set and first set of thermographs.

As referenced in the flowchart of FIG. 1, the method 100 may include an initial Step 102 of recording the distribution of body surface temperature with a passive imaging device 202. The passive imaging device 202 may include, without limitation, an infrared imaging device and a thermograph. Those skilled in the art will recognize that the passive imaging device 202 and the thermograph are non-invasive measuring instruments that produce a trace or image representing a record of the varying temperature or infrared radiation over an area or during a period of time. Thermographs, or infrared imaging system, have been in use for many years, mainly in connection with breast cancer detection and imaging.

The method 100 detects the inflammation by initially identifying at least one hot area 206, at least one hot line 208, and at least one hot acupoint 210 on the surface of the body. These hot region detected by utilizing a passive imaging device 202, such as an infrared or thermograph, to capture a thermograph image on the surface of the body. The thermograph image may display at least one hot region on the body. The hot region may be indicative of inflammation in an internal organ within the body.

The inflamed or potentially cancerous internal organs and components of the body may include organs such as heart, liver, spleen, lung, kidney, stomach, small intestine, large intestine, bladder, pancreas, etc. It is significant to note that an inflamed, unhealthy internal organ may be caused by various maladies, including, without limitation, arthritis, rheumatoid arthritis, allergy, asthma, tumors, pneumonia, abnormal degeneration of the brain, nerve system, blood circulatory systems, gland, gum diseases, etc. Further, the internal inflammation may be a symptom of pain such as from migraine, fibromyalgia, neck pain, back pain, joint pain, leg pain, hand pain, kidney, etc.

The method 100 further includes a Step 104 of utilizing a meridian theory of traditional Chinese medicine for identifying at least one hot area 206, at least one hot line 208, and at least one hot acupoint 210 along a meridian pathway, wherein the at least one hot area 206, the at least one hot line 208, and the at least one hot acupoint 210 are at least partially indicative of at least one internal organ of the body having an internal inflammation.

Those skilled in the art will recognize that at least one meridian pathway is defined by a network that interconnects the at least one internal organ. In some embodiments, at least one meridian pathway may include, without limitation, a stomach meridian, a gallbladder meridian, a large intestine meridian, a heart meridian, and a kidney meridian.

Figure 4:
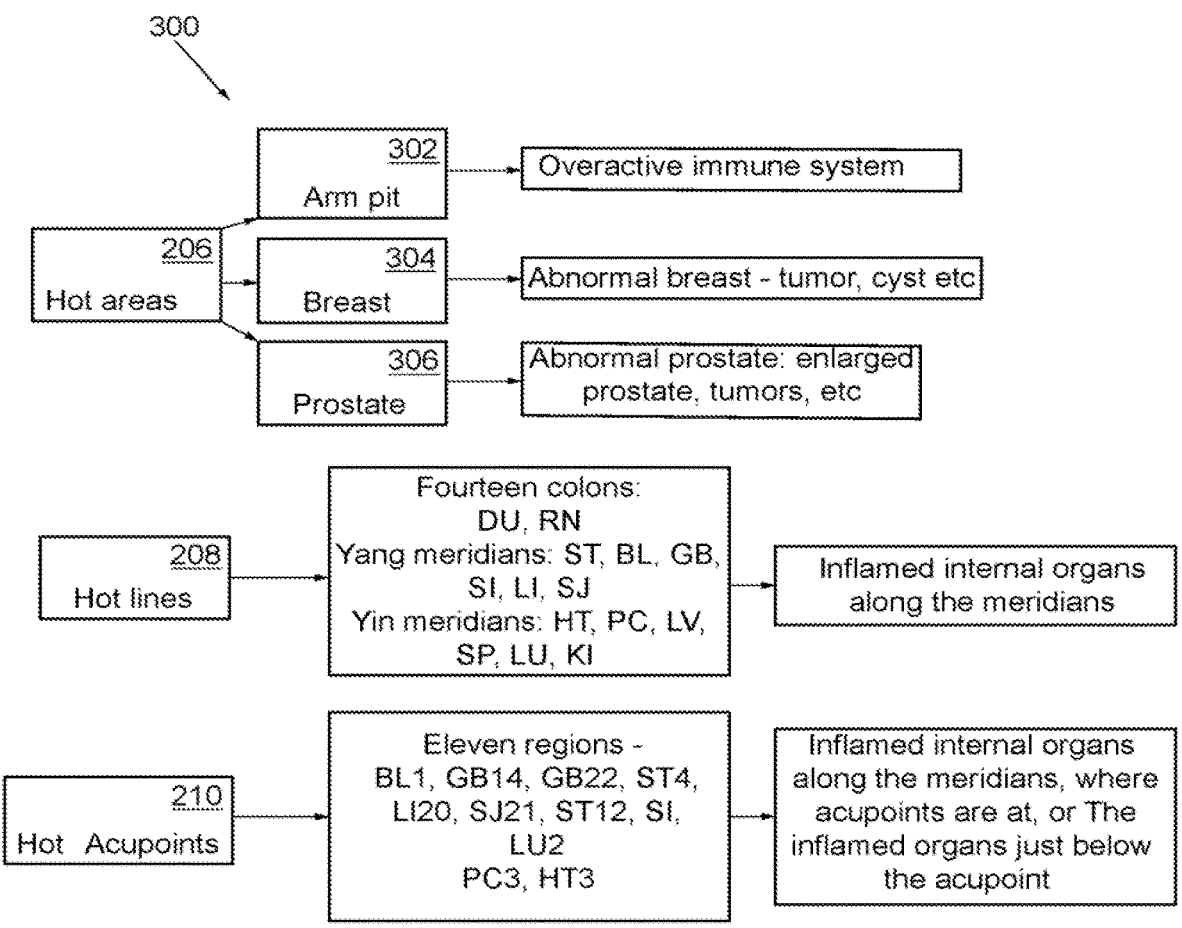
FIG. 4 illustrates a diagram illustrating an exemplary process of the healing effects at different durations of the imaging, in accordance with an embodiment of the present invention.

The method 100 also identifies at least one hot acupoint 210 that is disposed along a meridian pathway of the body. Referring to FIG. 4 of the drawings, there are many acupoints which show up frequently as hot spots on the thermographs. These hot acupoints 210 may include, without limitation, are BL1, GB14, ST 4, ST 12, LI20, SJ21, LU 2, PC3, and HT3. They indicate there are inflamed or potentially cancerous internal organs along the meridians, where the hot acupoints belong. The inflammation acupoints PC3, and/or HT3 indicates the possible development or occurrence of cardiac vascular diseases.

Those skilled in the art will recognize that there are eleven regions in thermographs that indicate whether there are hot areas or hot spots, corresponding to acupoints and meridians. The twelve areas may include, without limitation, left and right front center ears: SJ 21; left and right inner point of the eyes: BL 1; left and right neck near the shoulder: SI meridian lines; left and right forehead temple area: GB14; left and right collar bone area: ST 12; and left and right arm pits: GB22. In summary, these acupoints are defined as six pairs; left and right (SJ21, BL1, GB14, ST12, GB22). There are in addition two hot areas which are related to organs beneath the body surface. They are the gut area and the reproductive organs.

In some embodiments, a Step 106 may include identifying the body surface temperature at the hot area 206, the hot line 208, and the hot acupoint 210, so as to determine an inflamed internal organ 212. Inflamed internal organs emit hot infrared radiation, which is transmitted preferentially along the meridian pathways and peaks at known acupoints that are close to the surface of the body. Thus, the method 100 essentially measures the degree of inflammation of the internal organ by the quantitative temperature at the acupoint at the surface of the body. In essence, internal organ abnormalities can be revealed by taking thermographs of the body and corresponding problematic organs with the meridian pathways.

A Step 108 comprises correlating a hot body surface temperature with a specific internal ailment. A color scheme provides a color to temperature correlation for this purpose. It is significant to note that the method 100 lies on the foundation that, based on the meridian theory of traditional Chinese medicine, the body surface temperature phenomena is connected to internal organs. The higher body surface temperature indicated by the hot spot is thus, a reflection of the temperature of the internal organs where the meridian pathways pass through. As measured by the infrared imaging device, hot spots and hot lines on the body surface reflect inflammation or cancer of the internal organs.

Thus, the nexus between the hot spot and the acupoint indicates a potentially inflamed or cancerous organ. This is because the meridian pathway serves as an optical fiber that channels the heat of internal organs to the surface of the body. Further, the infrared imaging device provides a non-invasive, passive, thermal detector that can be taken in seconds without disturbing the body's state of health. The thermal image can be taken before and a few minutes after treatment to determine the effectiveness of the treatment. If the treatment for a particular organ is not effective, the temperature along its corresponding meridian will not be changed. Hence, the effectiveness of treatment can be assessed with the infrared imaging device.

The method 100 may include a further Step 110 of administering a predetermined amount of a solid water particle to the hot area, the hot line, and the hot acupoint regions of the body to assist in healing the internal ailment. Once the nexus between the hot area, hot line, and hot acupoint and the acupoint and meridian pathway has been discerned, the treatment commences. The treatment may include administrating a predetermined amount of solid water particle to the body with a delivery system. In one embodiment, the SWP consists of only pure water molecules and no other chemicals and generally does not have harmful side effects. The SWP may include, without limitation, stable water clusters, polydihydrogenoxide, and IE. The delivery system comprises at least one of the following: oral administration, topical administration, vapor administration, and intravenous administration.

The solid water particle may be administered on the surface of the body through a delivery means, such that healing of the inflamed internal organ is attempted. The delivery means may include at least one member selected from the group consisting of oral administration, topical administration, vapor administration, and intravenous administration.

In some embodiments, the oral administration may include a liquid, a capsule, or a gel consisting of the predetermined quantity of solid water particles. The topical administration may include a cream consisting of the predetermined quantity of solid water particles. The vapor administration may include a nebulizer and an inhaler consisting of the predetermined quantity of solid water particles. The intravenous administration may include an intravenous injection consisting of the predetermined quantity of SWP.

In one possible embodiment, the mechanism of healing by SWP may be explained simply as follows: meridians are hypothesized to consist of solid water particles SPW (includes those of double helix shape). The malfunction of organs along meridians is explained in Chinese medicine as the blocking of the flow of qi along the meridians. By drinking SWP, the charged water particles repair the meridian and unblock it, so that qi can freely flow again.

In one embodiment, the delivery system $D_\alpha$ that delivers the solid water particles, to the subject under treatment comprises four kinds of delivery systems, which are denoted as $D_\alpha$ with $\alpha$=d, c, b, and v, where "d" means digestive system, "c" means cream, "b" means breathing, and "v" refers to intravenous injection.

The $D_d$ intake of SWP to digestive system can take the form of drinking a glass of SWP, or pills or gels with SWP. The SWP is taken via the mouth, and primary to the digestive system. Some will be absorbed in the mouth to the bloodstream directly.

Further, the $D_c$ intake of SWP is carried through the skin via a topical cream, which consists of SWP.

The $D_b$ intake of SWP through the breathing may be done by nebulizer or inhaler, or any other device. The SWP will go directly upward to the brain and downward to the lung without going through the stomach as in the method 100 of $D_d$.

The $D_v$, intake of SWP through the intravenous method 100 goes directly into the blood stream.

In one exemplary administration, the cream is applied at least topically to at least one member selected from the group consisting of: the left and right front center ears, the left and right inner point of the eyes, the left and right neck near the shoulder, the left and right forehead temple area, the left and right collar bone area, the left and right arm pits, and an SI line segment at the bottom of the neck though other areas of the body may also receive treatment.

A final Step 112 comprises determining the healing effects on the internal ailment of the organ 212 by calculating multiple body surface temperatures over a duration. The healing effects are discerned by calculating multiple passive images over a duration. The duration of the hot region indicates the stage at which healing is occurring. Specifically, Detection of healing effect from treatment: In order to see the effect healing from treatment, it is necessary to take more than one set of thermographs. The first set of thermographs at time $t_1$ 402 is to detect the inflammation of internal parts. The temperature is given by the passive image 204 at the position x, and y at time $t_1$ 402 for $\alpha$, which can be an area, line, or points. The accuracy of the current commercial infrared camera system is less than 0.1° Celsius.

$$T_\alpha(x,y;t_1)$$

Then after a short duration, about 15 minutes to 30 minutes another set of thermographs are taken at time $t_2$ 404. Significant changes of temperature in hot areas, hot lines, and hot spots indicate healing has taken. The temperature of the second set thermographs is denoted by:

$$T_\alpha(x,y;t_2).$$

The change of temperature at x,y, is their differences:

$$\Delta T_\alpha(x,y)=T_\alpha(x,y;t_2)-T_\alpha(x,y;t_1).$$

The statistical fluctuation of skin temperature is about 0.1° Celsius. So if the absolute value of the temperature difference i $\Delta T$ s greater than 0.3° Celsius, then the change of temperature is three standard deviations away. Thus, rather than measuring and calculating with each image, the color scheme of the passive image is beneficial. The change of color is about 1° Celsius. There may be three shades of color. So the change of shade of color is detected, which means a change of temperature of 0.3° C., then the change is statistically significant.

The solid water particles discussed above function to unblock the meridian channel and allow qi and blood to flow freely to the inflamed area, the inflamed area generally gets even hotter. If the inflammation is not serious, healing occurs. In 15 minutes, inflammation is generally reduced. If the inflammation is serious, the healing occurs but is not sufficient. Thus, the inflamed area becomes hotter after 15 minutes. Whether the area gets hotter or colder, healing has occurred. However, for the healing to be successful, it should cool down eventually. So often time a third set of thermograph at time $t_3$ 406 is needed to confirm that healing is successful. In addition, the solid water particles actively prevent the development of cancers through this unblocking of the meridian channel.

$\Delta T_\alpha(x,y)=T_\alpha(x,y;t_3)-T_\alpha(x,y;t_1)$, where the difference of temperature is between the third set and first set of thermographs.

whereas $\Delta T_\alpha < 0.3°$ Celsius is insignificant, and $\Delta T_\alpha > 0.3°$ Celsius is statistical significant.

In one exemplary use of the method 100, an infrared imaging device captures multiple infrared images over a duration. The infrared images may be referred to as thermographs, of the body. In theory, when a person is of perfect health, the detected body surface temperature is uniform and generally cool, with few if any hot spots. However, in reality, most bodies have problems, and thus surface body temperature often comprises an uneven distribution of hot and cold acupoint temperatures. The hot areas are considered here.

Often, there are hot spots, hot lines, and hot acupoints. These hot regions can be identified with acupoints, and many hot lines can be identified with meridians. It has been found experimentally that infrared travels much preferable along meridian than perpendicular by hundreds of times. In essence, the meridians can be regarded as a fiber optics that can transmit heat, or infrared radiation from an inflamed or cancerous internal body part to other parts of the body. When the meridians are close to the body surface, the heat will be seen by infrared images.

Thus, taking thermographs images 204 at the surface of the body reveals the existence of meridians. It is safe to consider this a direct proof of the existence of meridians. Conversely, the hot spots and hot lines denoted in the infrared images reflect that there are inflammations inside parts of the body. This is schematically shown in the FIG. 2 diagram as the detection of internal inflammation or preliminary stages of cancer or cardiac vascular diseases.

Figure 2:
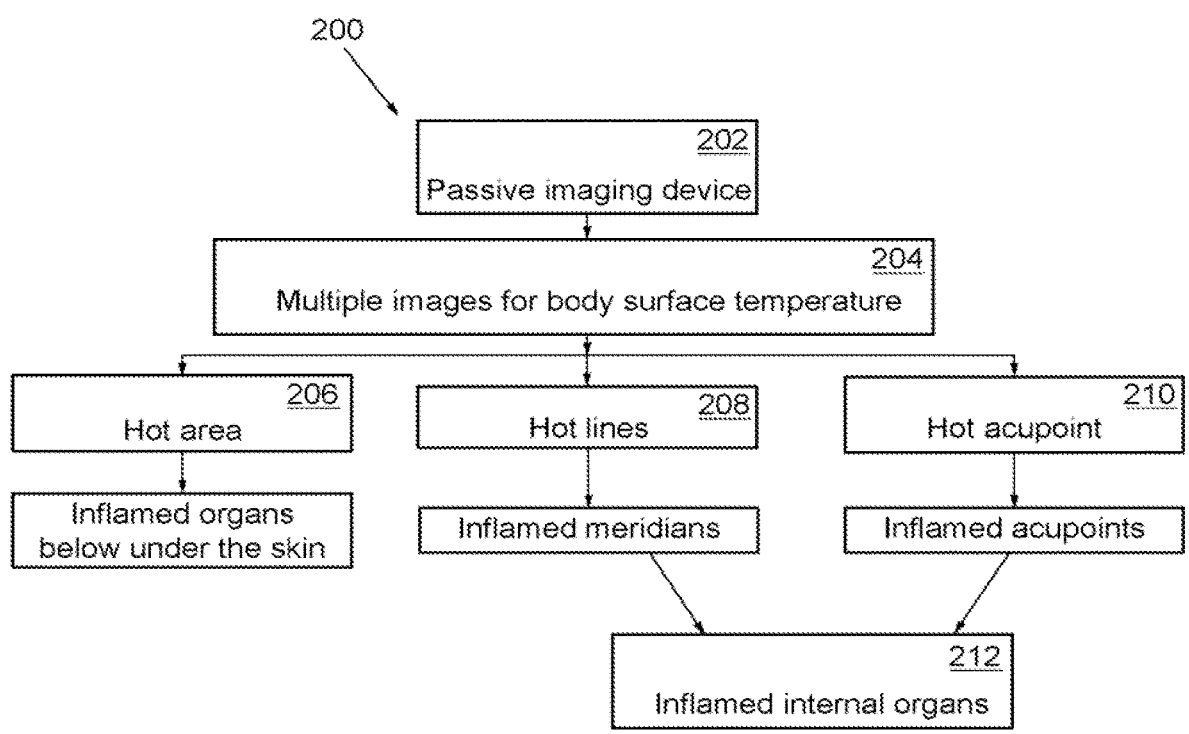
FIG. 2 illustrates a diagram illustrating an exemplary process of the passive imaging device detecting hot regions on the surface of the body, in accordance with an embodiment of the present invention.

FIG. 2 illustrates a diagram illustrating an exemplary process 200 of the passive imaging device 202 for detecting hot regions on the surface of the body. The passive imaging device 202, such as an infrared camera takes at least one infrared image 204, also known as thermographs, to see the distribution of body surface temperature. The hot regions of the body often reflect an inflamed organ 212 below the skin. There are three kinds of hot domains: at least one hot area 206, at least one hot line 208, and at least one hot acupoint 210. In one embodiment, the hot line 208 represents inflamed meridians, and the hot acupoint 210 represents inflamed acupoints.

FIG. 4 illustrates a diagram illustrating an exemplary process 300 of the correlation between the hot regions of the body with internal inflammations. The correspondence of hot area 206 with inflammation of internal organs or overactive system. It is known in the art that there are three most obvious hot regions of the body that indicate inflamed or cancerous organs and general health problem. The hot area 206 comprises a hot arm pit 302 indicating an overactive immune system, a hot breast 304 indicating an abnormal breast, which may indicate tumors, cyst, etc., and a hot prostate 306 area indicating abnormal prostate, which may be enlarged prostate and/or tumors.

FIG. 3 illustrates a diagram illustrating an exemplary process 400 of the healing effects at different durations of the imaging. The healing occurs through a self-healing mechanism. The healing medium referenced in process 400 includes water infused with solid water particles (SWP). Those skilled in the art will recognize that SWP is not a drug, and SWP is not like normal healing with the drug, where the drug directly works on the bacteria. The chief function of the SWP is to enable qi (energy), and blood to flow freely. Consequently, the inflamed cells, the organs, and internal organs gain sufficient nutrients to cure the cause for the inflammation or prevent the development of cancer.

As the process 400 illustrates, the healing of the inflammation can be quantified by capturing multiple sets of thermograph images. The first set of thermograph images are taken at a first time $t_1$ 402, and show inflammation occurs on the body surface. In the standard visual color used for the thermograph, the changing of hot color to red (hot), white (hotter), and green (healthy) indicates the inflammation probability for that region. Specifically, the process shows healing of the internal inflammation by correlating at least one hot area, the at least one hot line, and at least one hot point with the inflammation.

The first set of thermographs at time $t_1$ 402 is to detect the inflammation of internal parts. The temperature is given by the passive image at the position x, and y at time $t_1$ 402 for α, which can be an area, line, or points. The accuracy of the current commercial infrared camera system is less than 0.1° Celsius. After about 15 minutes to 30 minutes, another set of thermographs are taken at time $t_2$ 404. Significant changes of temperature in hot areas, hot lines, and hot spots indicate healing has taken. The temperature of the second set thermographs are denoted by: $T_\alpha(x, y; t_2)$ The change of temperature at x,y, is their differences. The statistical fluctuation of skin temperature is about 0.1° Celsius. So if the absolute value of the temperature is greater than 0.3° Celsius, absolute $(\Delta T) > 0.3°$ Celsius, then the change of temperature is three standard deviations away. Thus, rather than measuring and calculating with each image, the color scheme of the passive image is beneficial. The change of color is about 1° Celsius. There may be three shades of color. So the change of shade of color is detected, then the change is statistically significant.

The solid water particles discussed above function to unblock the meridian channel and allow qi and blood to flow freely to the inflamed area, the inflamed area generally gets even hotter. If the inflammation is not serious, healing occurs. In 15 minutes, inflammation is generally reduced. If the inflammation is serious, the healing occurs but is not sufficient. Thus, the inflamed area becomes hotter after 15 minutes. Whether the area gets hotter or colder, healing has occurred. However, for the healing to be successful, it should cool down eventually. So often time a third set of thermograph at a time $t_3$ 406 is needed to confirm that healing is successful.

Referring to FIG. 4 of the drawings, the hot lines 208 define about fourteen meridians. The fourteen meridians consist of DU meridian and Ren meridian plus six yang meridians and six yin meridians. The six yang meridians are stomach meridian ST, Bladder meridian BL, Gallbladder meridian GB, Small Intestine meridian SI, Large intestine meridian LI, and Triple heater meridian SJ. The six yin meridians include, without limitation, a heart meridian HT, a pericardium meridian PC, a liver meridian LV, a spleen meridian SP, a lung meridian LU, and a kidney meridian KI. The hot meridian lines indicate they are inflamed and potentially cancerous internal organs along with other parts of meridians. The inflamed heart meridian and/or pericardium meridian, and their acupoints HT3 and/or PC 3 indicate the possibility of cardiac vascular diseases.

Furthermore, the body has numerous acupoints which show up frequently as hot spots on the thermograph images. These hot acupoints may include, without limitation, are BL1, GB14, ST 4, ST 12, LI20, SJ21, LU 2, PC3, and HT3. They indicate there are inflamed internal organs along the meridians, where the hot acupoints belong.

Figure 5A:
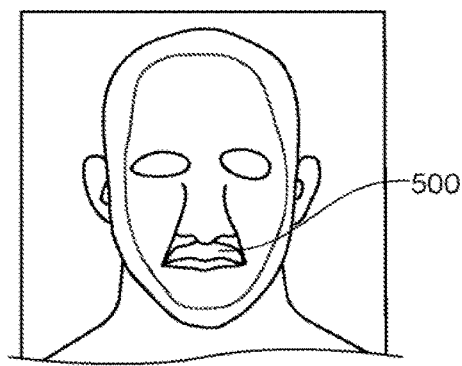
FIG. 5A illustrates an idealized and FIG. 5B exemplary stomach meridians and acupoints viewed through an infrared imaging device, in accordance with an embodiment of the present invention.
Figure 5B:
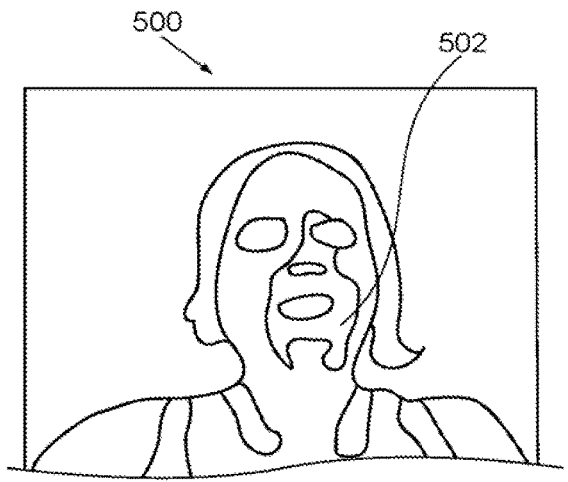

FIGS. 5A and 5B illustrate exemplary thermograph image 500 of a stomach meridian line 500 and at least one hot acupoint (ST4) 502 viewed through a passive imaging device 202. In some embodiments, the passive imaging device 202 can only see a segment of meridians that are close to the skin surface. However, FIG. 5A illustrates the idealized stomach meridian line 500 on the surface of two sides of the nose that can be seen via an infrared imaging system. FIG. 5B references the thermographs taken by a passive imaging device 202.

Figure 6A:
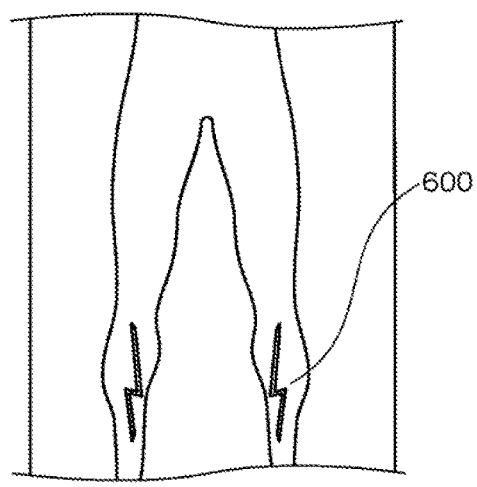
FIG. 6A illustrates an idealized and FIG. 6B exemplary thermographs of the stomach meridians and acupoints shown in FIGS. 5A and 5B, in accordance with an embodiment of the present invention.
Figure 6B:
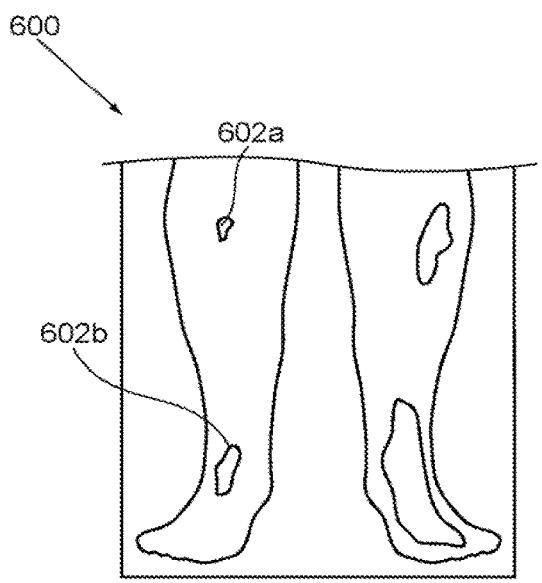

FIGS. 6A and 6B illustrate exemplary thermograph image 600 of the stomach meridian line and at least one acupoint shown in FIGS. 5A and 5B. In some embodiments, the passive imaging device 202 can only see a segment of meridians that are close to the skin surface. However, FIG. 6A illustrates the idealized stomach meridian 600 on the surface of the front part of the legs that can be seen via the passive imaging device 202. FIG. 6B references the thermographs of two white-hot acupoints 602a, 602b taken by a passive imaging device 202.

Looking at thermograph of a body, each pixel of the thermograph image 204 has an accurate numerical temperature. For example, a thermograph image 204 that has a 1000×1000 pixel means that there are 100,000 numerical values that characterize the surface temperature of the body. Often, a color scheme is used to help decipher the various temperatures.

Figure 7:
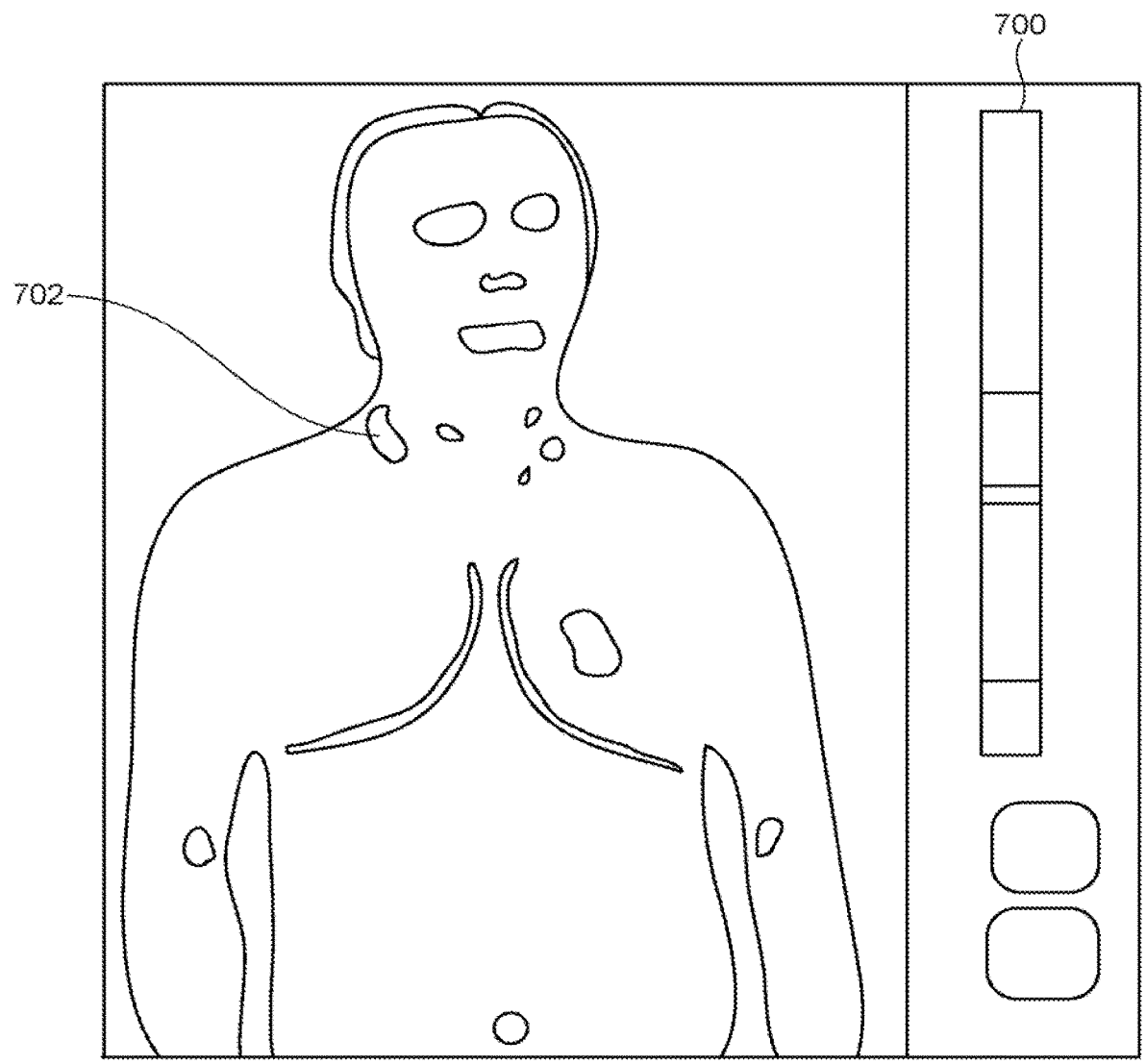
FIG. 7 illustrates exemplary correspondence of color scheme and temperature of the thermographs shown in FIG. 5A, FIG. 5B, FIGS. 6A and 6B, in accordance with an embodiment of the present invention.

FIG. 7 illustrates exemplary color scale 700 for correspondence of color scheme and temperature of the thermograph image shown in FIGS. 6A and 6B. For better understanding and analysis, all thermographs are shown in color with heat differentiation. The temperature range corresponds with the color the thermographs show. The hottest spot or line 702 is white, as shown in FIG. 7. However, as the temperature progressively cools; the color pattern goes from red, yellow, green, blue and black as the coldest. The color scale 700 is adjusted so that the green color implied a healthy state and the other colors of yellow, red, and white representing inflamed tissue.

In analyzing all of the thermograph images 204, attention is focused mainly on the very hot areas, which in the present scheme is red and/or white, with white being the most inflamed. A hot temperature along a meridian line is interpreted to be inflammation of or preliminary development of cancer in organs and tissues along that meridian, and is considered to be in an unhealthy state. In one possible embodiment, the correspondence of color scheme with temperature at the hot regions is as follows: white is the hottest about 34° Celsius, red is about 33° Celsius, yellow about 32° Celsius, and green about 31° Celsius, blue about 28° Celsius, and black the coldest 26° Celsius.

In some embodiments, the green color is adjusted to represent healthy state on the surface of the body, which is about 30 to 31° Celsius. The white color is 3° C. higher is about 34° C. The red color represents temperature about 33° C. or about 2-3° Celsius is higher than normal temperature. Thus, red represents moderate inflammation. The yellow color is about 32° Celsius, or 1° Celsius above normal, which is tolerable. The attention is generally on white and red color in thermograph, which is equivalent to a body having a fever of 40 Celsius and 39° Celsius. The exact correspondence is shown on FIGS. 7, 10A, 10B.

In analyzing the thermal images 204, there are six colors in these thermal images: white, then hottest, then red, yellow, green, blue and black that span 8° C. From one color to another color there is a change of about 1.0° C. Within each color, there are three distinguishable shades. So, when a different shade of color is observed, it is a change of about 0.3° C. The statistical fluctuation of skin temperature is about 0.1° C. So when a color shade is observed it is three standard deviations away, and, hence, statistically significant, provided that all other conditions remain constant in the 15 minutes duration.

Figure 8A:
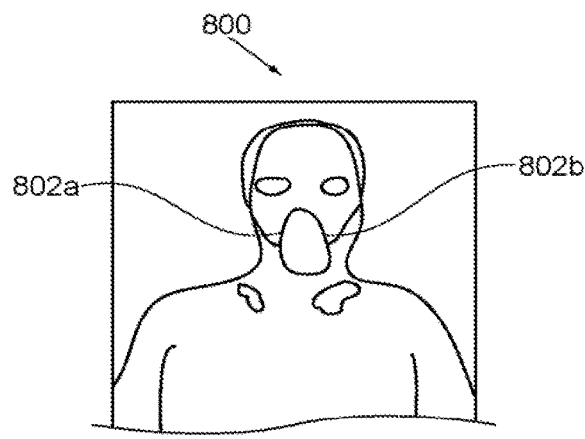
FIGS. 8A and 9A illustrate exemplary thermographs of the stomach meridians and acupoints for an internally inflamed stomach before administering solid water particles, in accordance with an embodiment of the present invention.
Figure 8B:
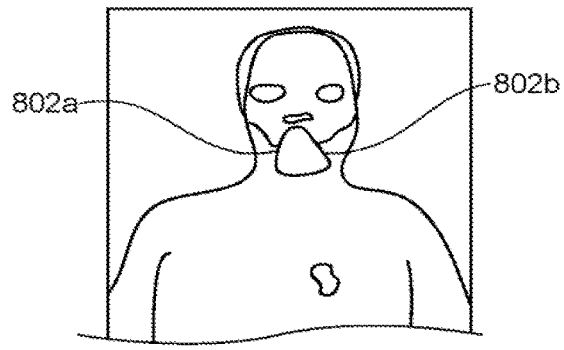
FIG. 8B and FIG. 9B illustrates exemplary thermographs of another part of the stomach meridians and acupoints for an internally inflamed stomach, fifteen minutes after administering solid water particles, in accordance with an embodiment of the present invention.

FIGS. 8A and 8B respectively illustrate exemplary thermograph images 800 of the stomach meridians and acupoints for an internally inflamed stomach before and after administering solid water particles. The head and the legs of a body showing stomach inflammation shows up as hot lines 802a, 802b besides the nose down to the sides of mouth, and close up under the mouth. These are standard Stomach Meridian segment which are known in the art to be displayed in any Meridian chart in an acupuncturist's clinic.

Figure 9A:
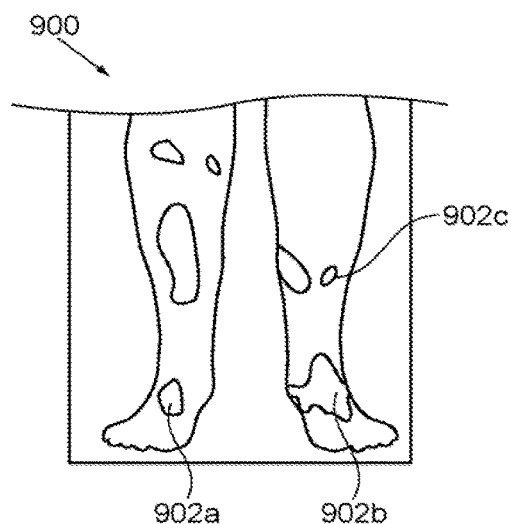
Figure 9B:
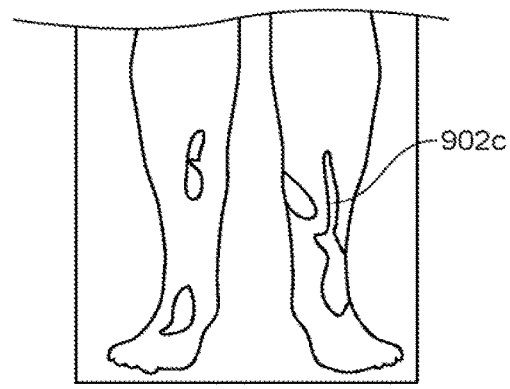

FIGS. 9A and 9B respectively illustrate exemplary thermograph images 900 of the stomach meridians and acupoints for an internally inflamed stomach shown in FIGS. 8A and 8B, fifteen minutes after administering solid water particles. The inflammation of stomach also carried by stomach meridian lines 902a, 902b, 902c to the legs, and show up as hot line in the front part of the two legs. These lines are not as neat as shown in the idealized stomach meridian shown in a Meridian Chart. Idealized and standardized human parts are shown in any anatomy text book. Those skilled in the art will recognize that the actual human parts are not standardized and much messier than what are shown in the standard anatomy text book. The same happens here in the realm of acupuncture and meridian lines.

In some embodiments, the inflammation in the stomach can be reduced by drinking water that contains SWP. The result is shown in FIGS. 9A and 9B. The temperature of hot line is reduced after drinking SWP in 15 minutes. The reduction of temperature of the hot lines 802a, 802b, 902a, 902b, 902c around the nose and mouth and on the front legs indicates that inflammation of the Stomach is reduced. The healing has occurred right away.

In some embodiments, the inflammation of the stomach is carried by the Stomach Meridian to show as hot lines around the nose and mouth as well as hot vertical lines on the front two legs. The left column pictures are taken before and the right column pictures are taken fifteen minutes after drinking the water that contains the SWP.

Figure 10A:
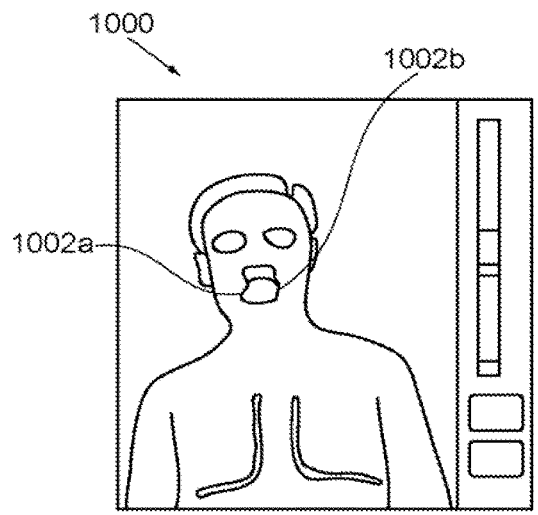
FIGS. 10A and 10B illustrate the exemplary color of the stomach meridians and acupoints for an internally inflamed stomach shown in FIGS. 8A and 8B, highlighting acupoints at the side of the mouth, in accordance with an embodiment of the present invention.
Figure 10B:
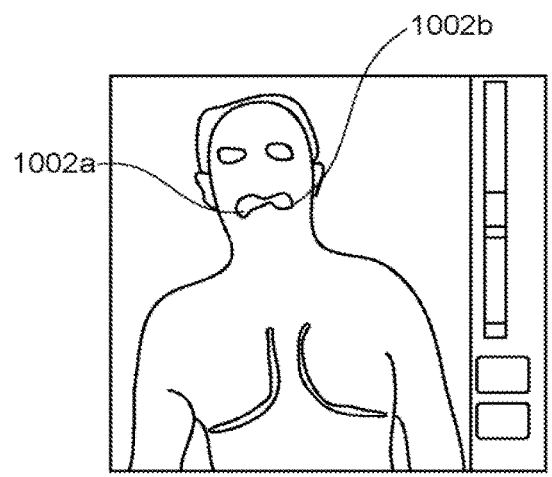

FIGS. 10A and 10B illustrate exemplary thermograph color images 1000 of the stomach meridians and acupoints for an internally inflamed stomach shown in FIGS. 9A and 9B, highlighting acupoints at the side of the mouth. In some embodiments, two white spots 1002a, 1002b at the two sides of the mouth are acupoints ST4. As FIG. 9B shows, the white spots 1002a, 1002b heat up about 15 minutes after drinking SWP. This illustrates the fast healing effect of SWP. In this instance, the SWP repairs the blockage in the meridians, which enable the qi and blood to flood to problem area to heal. If the problem is serious, it would stay there and show heating up. Generally after a long period of using SWP, the inflammation cools down, and see the problem starts to go away.

Figure 11A:
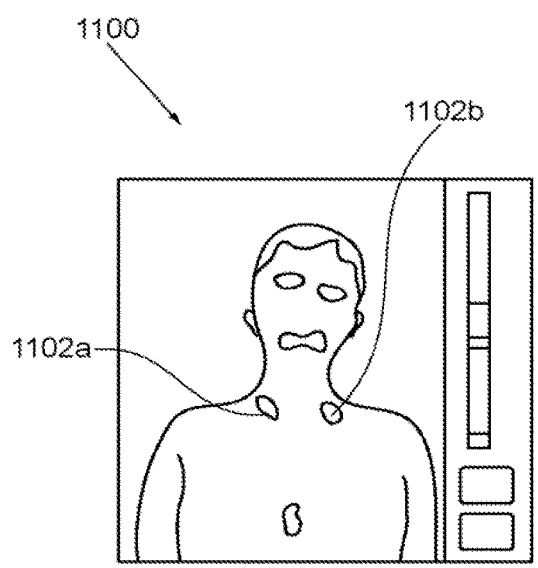
FIGS. 11A and 12A illustrate exemplary thermographs of thyroid meridians, which is at acupoint ST12 of stomach meridian, in accordance with an embodiment of the present invention.
Figure 11B:
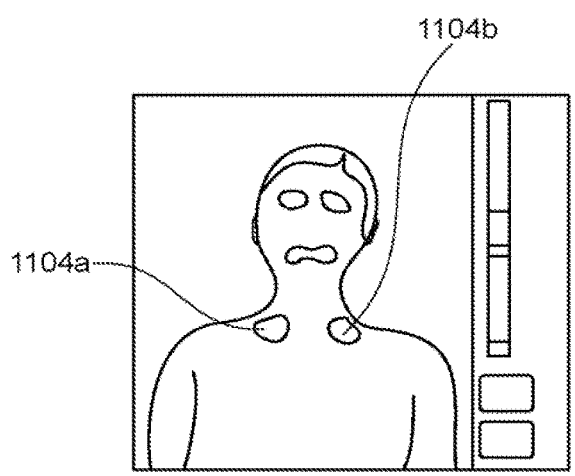
FIGS. 11B and 12B illustrate exemplary thermographs of the thyroid, which is at acupoint ST12 of stomach meridian, shown in FIGS. 11A and 12A, fifteen minutes after administering solid water particles, in accordance with an embodiment of the present invention.

FIGS. 11A and 11B illustrate exemplary thermograph images 1100 of thyroid acupoints. In some embodiments, the inflammation of thyroid shows up as hot acupoint ST 12. Before administering the SWP, the inflammation of thyroid is shown as white hot spots 1102a, 1102b on top of the collar bone (FIG. 11A). Approximately fifteen minutes after drinking SWP 15 minutes, the inflammation reduces, and the white spot becomes cooler, yet still hot the white spots become red spots 1104a, 1104b as shown in FIG. 11B.

Figure 12A:
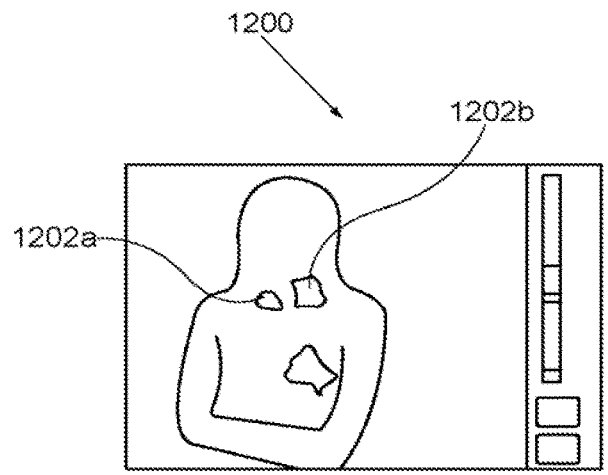
Figure 12B:
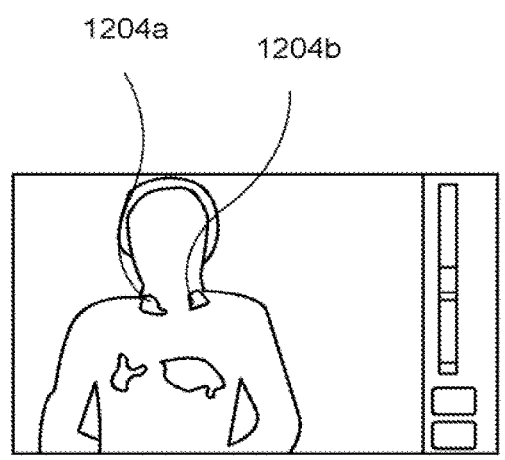

FIGS. 12A and 12B illustrate exemplary thermograph images 1200 of the thyroid and acupoints shown in FIGS. 11A and 11B, fifteen minutes before and after administering solid water particles. Before administering the SWP, the inflammation of thyroid is shown as white hot spots 1202*a*, 1202*b* on top of the collar bone (FIG. 12A). Approximately fifteen minutes after drinking SWP 15 minutes, the inflammation reduces, and the white spot becomes the cooler, yet still hot the white spots become red spots 1204*a*, 1204*b* as shown in FIG. 12B.

Figure 13:
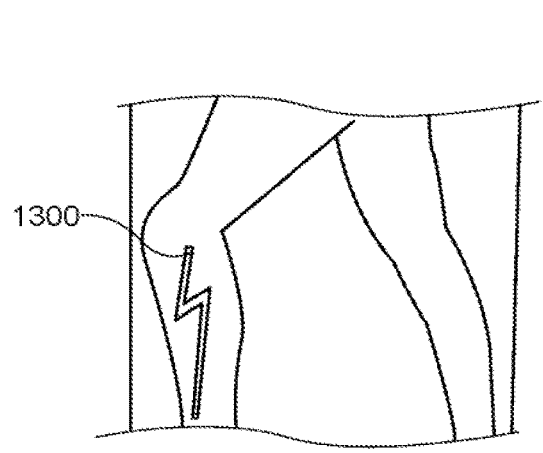
FIG. 13 illustrates an exemplary gallbladder meridian viewed through an infrared imaging device, in accordance with an embodiment of the present invention.
Figure 14:
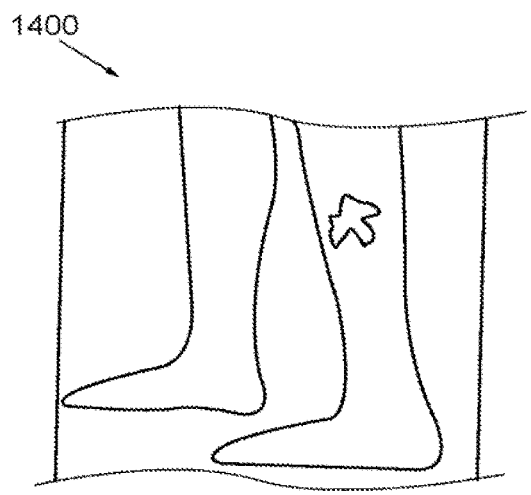
FIG. 14 illustrates an exemplary thermograph of the gallbladder meridian shown in FIG. 13, in accordance with an embodiment of the present invention.

FIG. 13 illustrates an idealized gallbladder meridian 1300 viewed through an infrared imaging device. FIG. 14 illustrates an exemplary thermograph image 1400 of the gallbladder meridian 1300 shown in FIG. 13.

An example of inflammation of gallbladder is shown in the thermograph image 1500 of FIG. 15A. Here, a white spot 1502 and red line 1504 are imaged on the outer leg. However, the inflammation is substantially reduced fifteen minutes after drinking SWP. Here the white area reduces significantly and the red line almost disappears. (FIG. 15B).

FIG. 16A shows the white spot from FIG. 15A has been substantially reduced, and the red line 1504 also reduced in size. Also, the red line disappears to become a yellow line 1602. FIG. 16B shows the white hot area disappear, the red line 1504 also reduced in size. FIGS. 17A and 17B illustrate exemplary color charts 1700 showing the correspondence of color scheme and temperature for the thermograph images 1600 shown in FIGS. 16A and 16B.

FIG. 18 illustrates an idealized large intestine meridian 1800*a*, 1800*b* viewed through a passive imaging device 202. In some embodiments, FIG. 19 illustrates an exemplary thermograph image 1900 of the large intestine meridian 1800*a*, 1800*b* shown in FIG. 18. Specifically, an idealized thermal image of the large intestine meridian 1800*a*, 1800*b* is shown. The thermograph image 1900 highlights two red spots 1800*a*, 1800*b* at the end of the nose (LI20), and the curved red line above the mouth. A realistic thermograph image 1900 of a body that has inflammation of the large intestine is illustrated in FIG. 19.

Figure 20A:
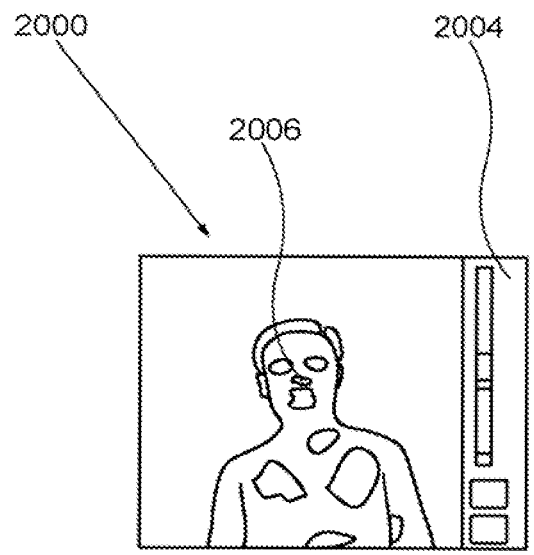
FIGS. 20A, 20B, 20C, and 20D illustrate exemplary thermographs of the large intestine meridian for an internally inflamed large intestine before and after administering solid water particles, in accordance with an embodiment of the present invention.
Figure 20B:
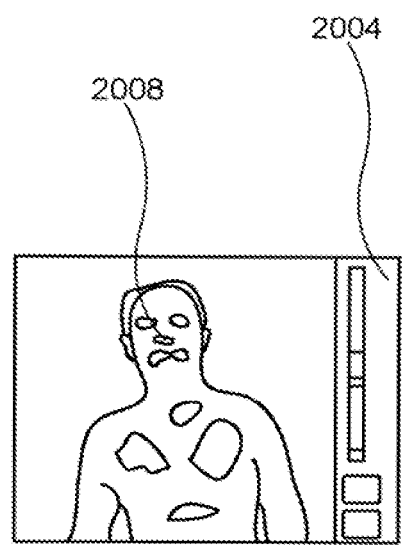

FIGS. 20A and 20B illustrate exemplary thermograph images 2000 of a large intestine meridian 2002 for an internally inflamed large intestine, both before and after administering solid water particles. FIGS. 20A and 20B also include a color chart 2004 that helps decipher the colors in the images 2000. The inflammation of colon is imaged as the inflammation of the large intestine meridian shown on the face above the mouth as well as across the belly. The top row red curved line 2006 above the mouth indicates the inflammation of the large intestine meridian, which in turn implies the inflammation of the large intestine. However, fifteen minutes after drinking SWP, the inflammation reduces the thick red curved line above the mouth 2006 becomes much thinner red line 2008.

Figure 20C:
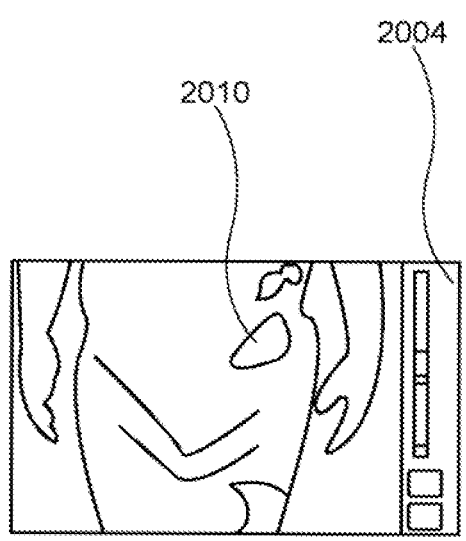
Figure 20D:
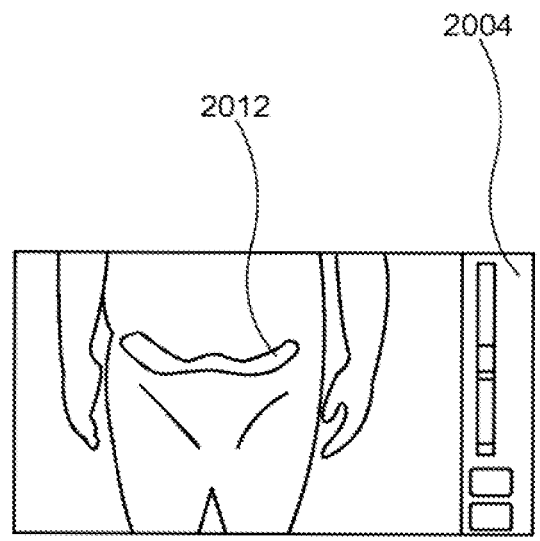

Turning now to FIGS. 20C and 20D, the inflammation of the colon often shows up a thick hot horizontal line 2010 across the belly. After 15 minutes drinking SWP, a substantial amount of the horizontal red line 2010 across the belly disappears, leaving a thinner red line 2012. The reduced red line 2012 indicates a reduction of inflammation for the colon.

Figure 21A:
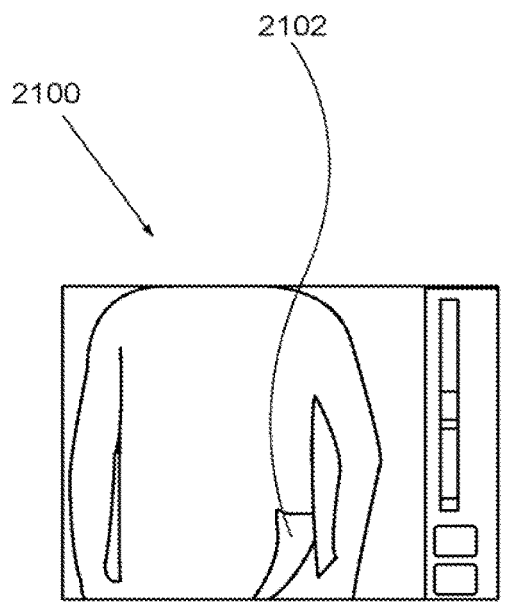
FIGS. 21A and 21B illustrate exemplary thermographs of the large intestine meridian for an internally inflamed large intestine showing up as a red line across the belly, before and after administering solid water particles, in accordance with an embodiment of the present invention.
Figure 21B:
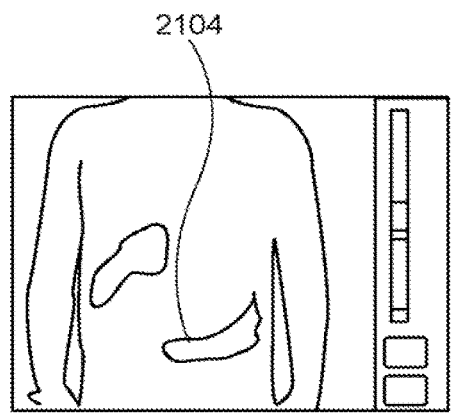

FIGS. 21A and 21B illustrate exemplary thermograph images 2100 of the large intestine meridian for an internally inflamed large intestine showing up as a red line 2102 across the belly, before and after administering solid water particles. The inflammation of the colon shows up as red line 2102 across the belly. However, fifteen minutes after administering the SWP, the red line 2102 almost completely disappears into a thin red line 2104, indicating the inflammation of the colon has reduced tremendously.

Figure 22:
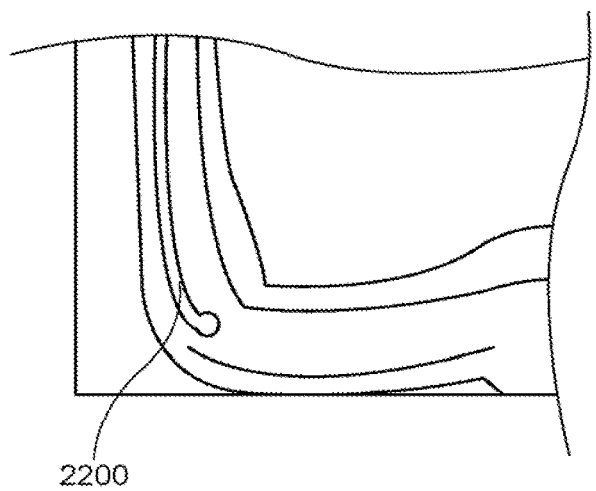
FIG. 22 illustrates an idealized heart meridian viewed through an infrared imaging device, in accordance with an embodiment of the present invention.
Figure 23:
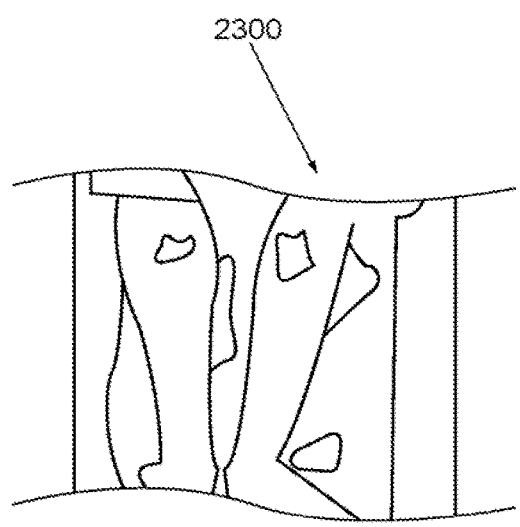
FIG. 23 illustrates an exemplary thermograph of the heart meridian shown in FIG. 22, in accordance with an embodiment of the present invention.

FIG. 22 illustrates an exemplary heart meridian 2200 viewed through an infrared imaging device. In some embodiments, the idealized heart meridian HT and its acupoints HT3 are shown as red line and red dot. FIG. 23 illustrates an exemplary thermograph of the heart meridian shown in FIG. 22. Specifically, FIG. 23 references the real thermograph image 2300 of a person with inflammation of the heart. The inflammation of the heart meridian may also indicate the possibility of cardiac vascular diseases.

Figure 24A:
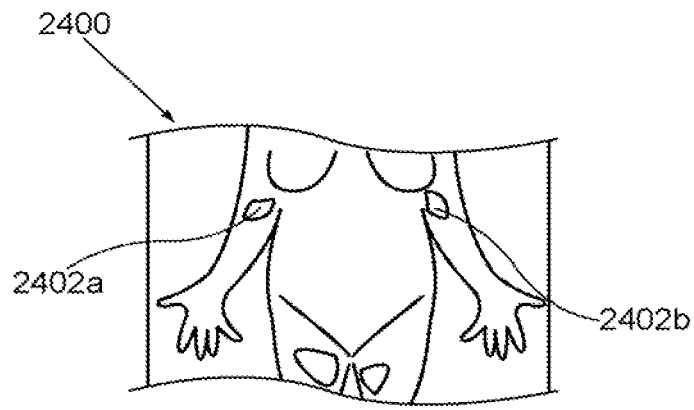
FIGS. 24A, 24B, and 24C illustrate exemplary thermographs of idealized heart meridians and acupoints, in accordance with an embodiment of the present invention.
Figure 24B:
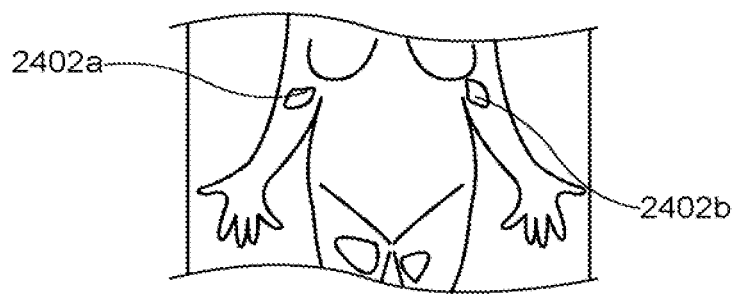
Figure 24C:
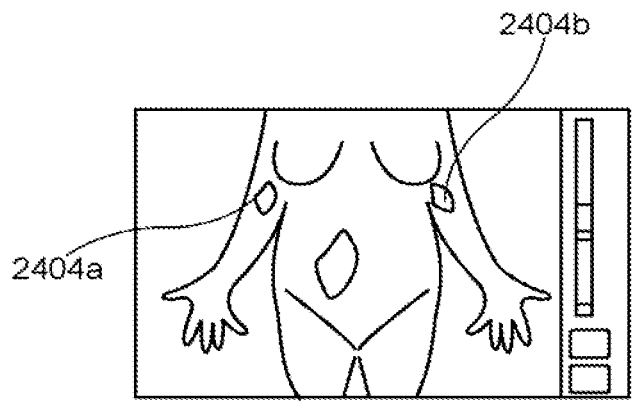
Figure 25A:
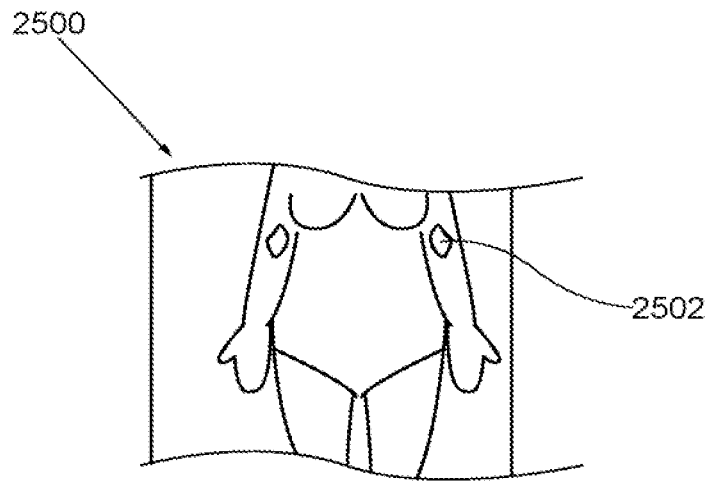
FIGS. 25A, 25B, and 25C illustrate exemplary thermographs of actual heart meridians and acupoints, in accordance with an embodiment of the present invention.
Figure 25B:
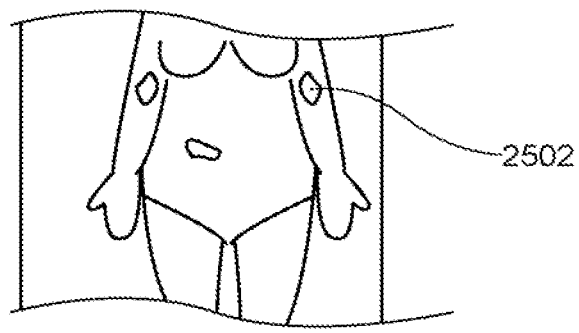
Figure 25C:
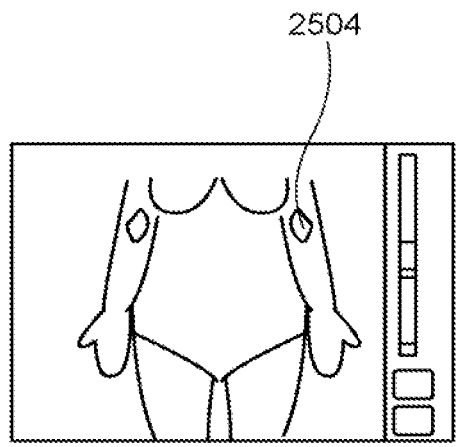

FIGS. 24A, 24B, and 24C illustrate exemplary thermograph images 2400 of idealized heart meridians and acupoints shown in FIG. 23. The illustration depicts gradual reduction and finally disappearance of two white dots 2402*a*, 2402*b* at acupoints HT and HT3 about fifteen minutes after administering the SWP. FIG. 24C illustrates red dots 2404*a*, 2404*b* that have replaced the white dots 2402*a*, 2402*b* after two weeks. Similarly, FIGS. 25A, 25B, and 25C illustrate exemplary thermograph images 2500 of actual heart meridians and acupoints. The illustration depicts gradual reduction and finally disappearance of the white dot 2502 at acupoints HT and HT3 about fifteen minutes after administering the SWP, and replacement with a red dot 2504. The inflammation of the heart meridian may also indicate the possibility of cardiac vascular diseases. The gradual reduction and disappearance of the white dot HT3, or PC3 and red line heart meridian means the prevention of cardiac vascular diseases. Cardiac vascular disease manifests itself as inflammation of the Heart meridian and/or Pericardia meridian and/or their acupoints HT3 and/or PC3. When there is no inflammation associated with Heart meririan, pericardia meridian, their acupoints, there is no cardiac vascular diseases.

Figure 26:
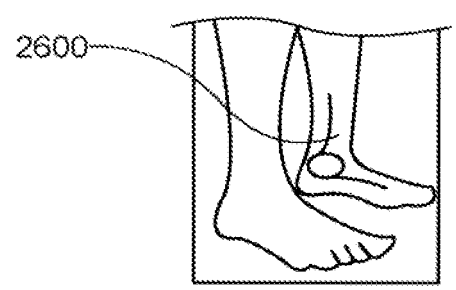
FIG. 26 illustrates an idealized kidney meridian viewed through an infrared imaging device, in accordance with an embodiment of the present invention.
Figure 27:
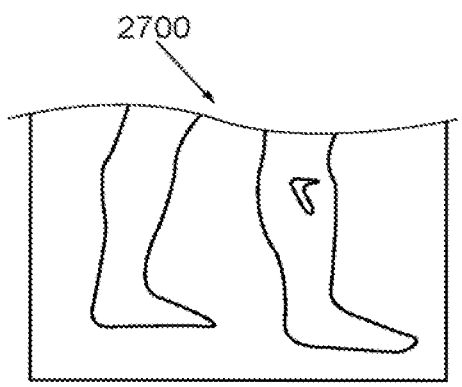
FIG. 27 illustrates an exemplary thermograph of the kidney meridian and acupoint shown in FIG. 26, in accordance with an embodiment of the present invention.

FIG. 26 illustrates an idealized kidney meridian 2600 viewed through an infrared imaging device 202. FIG. 27 illustrates an exemplary thermograph image 2700 of the kidney meridian and acupoint shown in FIG. 26. Specifically, FIG. 27 references the real thermograph of a person with inflammation of the kidney.

Figure 28A:
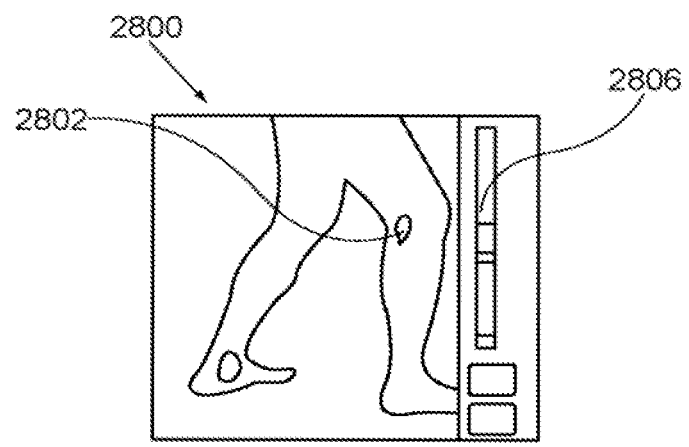
FIGS. 28A, 28B illustrate exemplary thermographs of kidney meridians and acupoints shown in FIG. 27, at the inner leg, before and after administering solid water particles, in accordance with an embodiment of the present invention.
Figure 28B:
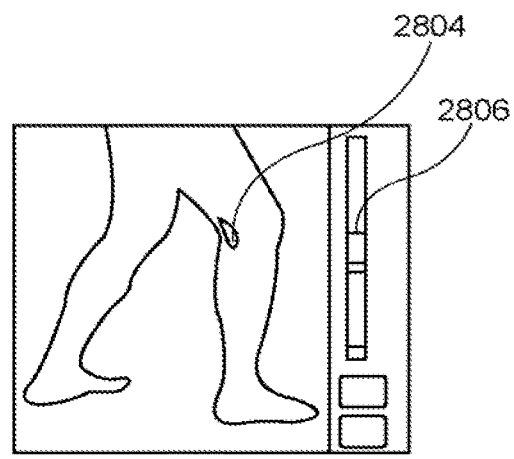

FIGS. 28A, 28B illustrate exemplary thermograph images 2800 of the kidney meridians 2600 and acupoints shown in FIG. 26, at the inner leg, before and after administering solid water particles. The illustration depicts gradual reduction and finally disappearance of the white dot 2802 at acupoints, about fifteen minutes after administering the SWP. A smaller white dot 2804 appears to indicate healing. A color chart 2806 helps decipher the colors in the images 2800.

Figure 29A:
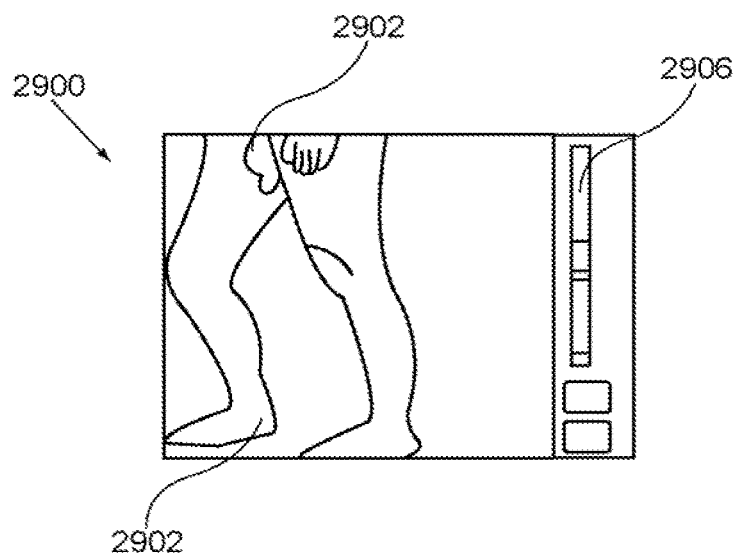
FIGS. 29A, 29B illustrate exemplary thermographs of kidney meridians and acupoints shown in FIG. 27, at the outer leg, before and after administering solid water particles, in accordance with an embodiment of the present invention.
Figure 29B:
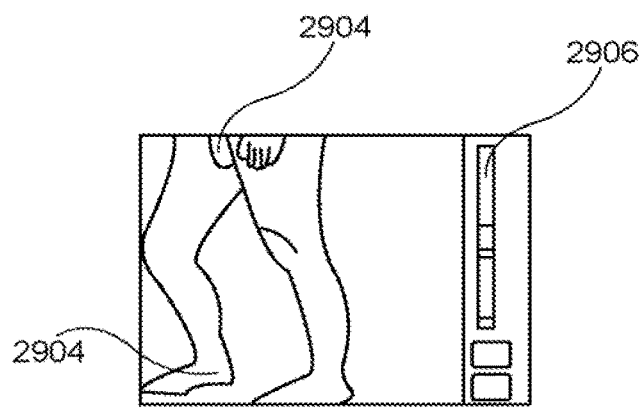

FIGS. 29A, 29B illustrate exemplary thermograph images 2900 of kidney meridians and acupoints shown in FIG. 27, at the outer leg, before and after administering solid water particles. The illustration depicts gradual reduction and finally disappearance of the white dot 2902 at acupoints, about fifteen minutes after administering the SWP. A smaller white dot 2904 appears after two weeks to indicate healing. A color chart 2906 helps decipher the colors in the images 2900.

Furthermore, it is important to point out cancer cells at an organ attract and consume more nutrients than normal cells. The oxidation of the nutrients of cancer cells will produce more heat, and manifests its presence as inflammation of the organ. The inflammation of the organ does not imply the existence of cancer cells, but the presence of cancer cells causes the inflammation of the organs. So, by reducing the inflammation of an internal organ, it prevents cancers from developing in that organ.

For example we see the inflammation of the colon via infrared imaging device. Drinking the solution with solid water particles reduces inflammation of the colon. This prevents the development of colon cancer.

Similarly, reduction of inflammation of the lung by drinking the solution of solid water particles prevents the development of lung cancer.

In addition, drinking the solution of solid water particles reduces the inflammation the breast prevents the development of breast cancer.

Reduction of inflammation of prostate (ovary, liver, etc.) by drinking solution of solid water particles prevents prostate (ovary, liver, etc.) cancer from developing.

In conclusion, the method 100 for detection and reduction of internal inflammation the prevention of cancer of an organ, and the prevention of cardia vascular diseases 212 combines passive images 204 and a meridian theory of traditional Chinese medicine. The method provides the steps of: recording the distribution of body surface temperature with a passive imaging device 202, such as an infrared imaging device; utilizing a meridian theory of Chinese medicine for identifying at least one hot area 206, at least one hot line 208, or at least one hot acupoint 210 along a meridian pathway; identifying the body surface temperature at the hot area 206, the hot line 208, or the hot acupoint 210, so as to determine an inflamed or cancerous internal organ 212; correlating a hot body surface temperature with a specific internal ailment; administering predetermined amounts of solid water particles to the hot area 206, the hot line 208, and the hot acupoint 210 regions of the body to assist in healing the internal inflammation; and determining healing effects of the internal inflammation by calculating multiple body surface temperatures over a duration.

Figure 30:
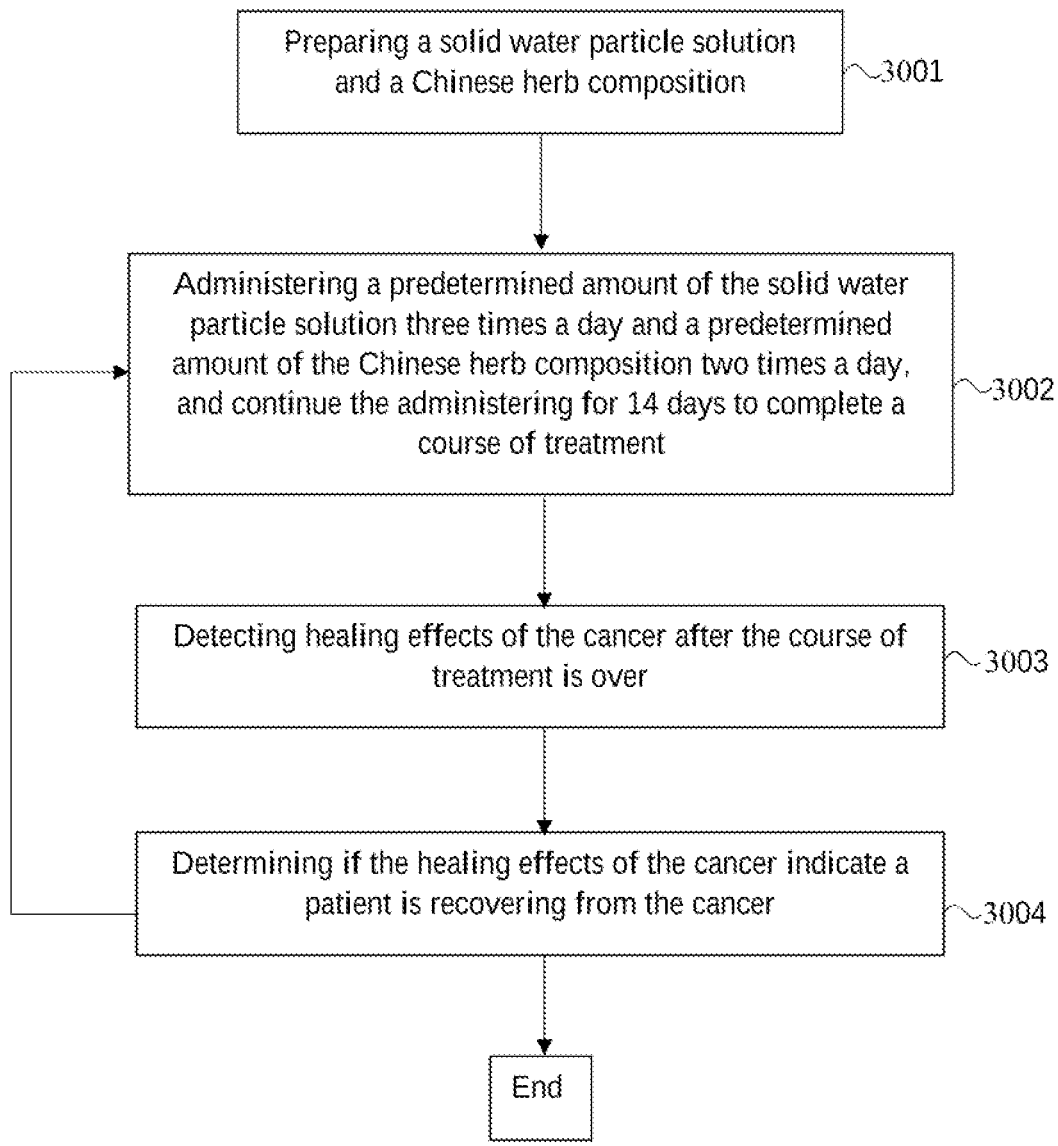
FIG. 30 illustrates a flowchart diagram of an exemplary method of treatment of cancer, in accordance with an embodiment of the present invention Like reference numerals refer to like parts throughout the various views of the drawings.

In addition, a method of treatment of cancer is referenced in FIG. 30. The method is based on administering both the solid water particles and the Chinese herb composition to avoid serious harm to the human body during the treatment of cancer through chemotherapy.

Step 3001: preparing a solid water particle solution and a Chinese herb composition. In this step, we must first prepare the solid water particle solution and the Chinese herb composition for the patient to administer. In this example, the Chinese herb composition consists of *Scutellaria barbata, Lobelia chinensis, Paris polyphylla, Prunella vulgaris, Artemisia capillaris*, Chinese Thorawax Root, White Peony Root, *Houpoea officinalis*, Indian Bread peel, Asiatic Plantain Seed, *Astragalus membranaceus, Angelica sinensis*, Dried Tangerine Peel, Common Burreed Rhizome, Blue Turmeric Rhizome, and Japanese Honeysuckle Stem. And when preparing the Chinese herb composition, a weight of every Chinese herb in the Chinese herb composition is between 4 and 5 grams to have a better healing effect when the Chinese herb composition is administered by the patient. However, a weight of the Chinese herb in the Chinese herb composition can be other than 4 and 5 grams, so it is not limited to this embodiment.

Step 3002: administering a predetermined amount of the solid water particle solution three times a day and a predetermined amount of the Chinese herb composition two times a day, and continue the administering for 14 days to complete a course of treatment. Through such a basic course of treatment, solid water particle solution combined with the Chinese herb composition can stimulate the human body's self-healing ability, thereby better treat the cancer and have a better healing effect. In this embodiment, the predetermined dosage of a solid water particle solution is at least 300 grams, the predetermined dosage of the Chinese herb composition is at least 60 grams, and a ratio of the predetermined amount of the solid water particle solution to the predetermined amount of Chinese herb composition is 5:1 to achieve a better healing effect, but it can also be other values and is not limited thereto. Moreover, the size of every solid water particle contained in the solid water particle solution can be 30 nm 1 micron. In this size range, the solid water particles contained in the solid water particle solution can be better absorbed by the human body, and achieve a better healing effect.

Step 3003: detecting healing effects of the cancer after the course of treatment is over. In this embodiment, healing effects are detected by taking blood test to determine whether the course of treatment is effective, but the healing effects can also be detected by other methods, so it is not limited to this embodiment.

Step 3004: determining whether the course of treatment is effective. If the healing effects of the cancer do not indicate a patient is recovering from the cancer, the patient will be asked to proceed with another course of treatment. In this embodiment, it would be a way to ask the patient to repeat the step 3002 to step 3004 until the healing effects of the cancer indicate a patient is not suffering from the cancer.

The present invention also provides a example of a patient is recovering from the liver cancer by utilizing this method provided in the present invention. The patient (hereinafter "Moonx") is recommended to accept hospice care only for comfort care by a doctor from city of xhope. However, after Moonx follow the steps in the method provided in the present invention and complete a course of treatment, Moonx is having a good healing effect and is gradually recovering from the liver cancer. Therefore, the method provided by the present application is proved to be effective.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What I claim is:

1. A method of treatment of cancer, the method comprising:
preparing a water cluster solution and a Chinese herb composition;
administering a predetermined amount of the water cluster solution at least two times a day and a predetermined amount of the Chinese herb composition at least two times a day, and continue the administering for 14 days to complete a course of treatment; and
determining healing effects for treating the cancer,
wherein the Chinese herb composition consists of *Scutellaria barbata, Lobelia chinensis, Paris polyphylla, Prunella vulgaris, Artemisia capillaris*, Chinese Thorawax Root, White Peony Root, *Houpoea officinalis*, Indian Bread peel, Asiatic Plantain Seed, *Astragalus membranaceus, Angelica sinensis*, Dried Tangerine Peel, Common Burreed Rhizome, Blue Turmeric Rhizome, and Japanese Honeysuckle Stem.

2. The method of claim 1, wherein the cancer is a biliary cancer or liver cancer.

3. The method of claim 2, wherein when administering the predetermined amount of Chinese herb composition, also administering the predetermined amount of the water cluster solution.

4. The method of claim 3, wherein a ratio of the predetermined amount of the water cluster solution to the predetermined amount of Chinese herb composition is 5:1.

5. The method of claim 4, wherein a weight of every Chinese herb in the Chinese herb composition is between 4 and 5 grams.

6. The method of claim 5, wherein a way for administering the predetermined amount of the water cluster solution is oral administration.

7. The method of claim 5, wherein a predetermined dosage of the water cluster solution is at least 300 grams.

8. The method of claim 7, wherein a predetermined dosage of the Chinese herb composition is at least 60 grams.

9. The method of claim 8, further comprising:
repeating the course of treatment until the healing effects indicate a patient is not suffering from the cancer.

10. The method of claim 8, further comprising:
proceeding with another course of treatment if the healing effects do not indicate a patient is recovering from the cancer.

11. The method of claim 9, wherein the other course of treatment comprises administering a predetermined amount of the water cluster solution five times a day and a predetermined amount of the Chinese herb composition two times a day, and continue the administering for 14 days.

12. The method of claim 6, wherein the oral administration comprises a liquid, a capsule, or a gel consisting of water clusters.

13. The method of claim 1, wherein the healing effects are determined by taking blood test.

14. The method of claim 1, wherein the course of treatment comprises administering a predetermined amount of the water cluster solution three times a day and a predetermined amount of the Chinese herb composition two times a day, and continue the administering for 14 days.

* * * * *